(12) United States Patent
Firat et al.

(10) Patent No.: US 9,738,932 B2
(45) Date of Patent: Aug. 22, 2017

(54) BIOMARKERS FOR CARDIOVASCULAR SIDE-EFFECTS INDUCED BY COX-2 INHIBITORY COMPOUNDS

(71) Applicants: Hueseyin Firat, Huningue (FR); Julie Boisclair, Somerville, MA (US); Olivier Grenet, Muttenz (CH); Elias Perentes, Muttenz (CH); Martin M. Schumacher, Sissach (CH)

(72) Inventors: Hueseyin Firat, Huningue (FR); Julie Boisclair, Somerville, MA (US); Olivier Grenet, Muttenz (CH); Elias Perentes, Muttenz (CH); Martin M. Schumacher, Sissach (CH)

(73) Assignee: FIRALIS SAS, Huningue (FR)

( * ) Notice: Subject to any disclaimer, the term of this patent is extended or adjusted under 35 U.S.C. 154(b) by 0 days.

(21) Appl. No.: 14/543,789

(22) Filed: Nov. 17, 2014

(65) Prior Publication Data
US 2015/0152501 A1    Jun. 4, 2015

Related U.S. Application Data

(62) Division of application No. 12/293,652, filed as application No. PCT/IB2006/000533 on Mar. 10, 2006, now abandoned.

(60) Provisional application No. 60/661,192, filed on Mar. 11, 2005.

(51) Int. Cl.
*C12Q 1/68* (2006.01)
*A61K 31/00* (2006.01)
*G01N 33/68* (2006.01)

(52) U.S. Cl.
CPC ............ *C12Q 1/6883* (2013.01); *A61K 31/00* (2013.01); *G01N 33/68* (2013.01); *C12Q 2600/106* (2013.01); *C12Q 2600/142* (2013.01); *C12Q 2600/158* (2013.01); *G01N 2800/328* (2013.01)

(58) Field of Classification Search
None
See application file for complete search history.

(56) References Cited

U.S. PATENT DOCUMENTS

| | | |
|---|---|---|
| 2006/0051873 A1 | 3/2006 | FitzGerald |
| 2010/0221186 A1 | 9/2010 | Firat et al. |

FOREIGN PATENT DOCUMENTS

| | | |
|---|---|---|
| EP | 2 287 608 A2 | 2/2011 |
| EP | 2 290 363 A1 | 3/2011 |
| EP | 1 910 825 B1 | 8/2012 |
| WO | WO 2004/112589 | 12/2004 |
| WO | WO 2006/023966 | 3/2006 |
| WO | WO 2006/095259 A2 | 9/2006 |

OTHER PUBLICATIONS

Fitzgerald, G.A., "Coxibs and Cardiovascular Disease," N. Engl. J. Med., 351(17), pp. 1709-1711, (2004).
Furberg, C.D., et al., "Parecoxib, Valdecoxib, and Cardiovascular Risk," Circulation, 111(3), p. 249, (2005).
Giannitsis, E., "Rationale for testing the cardiovascular risk for patients with Cox-2 inhibitors on the basis of biomarker NT-proBNP," Clinical Laboratory, vol. 51, No. 1-2, pp. 63-72, (2005).
Juni, P., et al., "Risk of cardiovascular events and rofecoxib: cumulative meta-analysis", The Lancet Limited, vol. 364, No. 9450, pp. 2021-2029, (2004).
Kanda, N., et al., "Cyclooxygenase-2 Inhibitor Enhances Whereas Prostaglandin $E_2$ Inhibits the Production of Interferon-Induced Protein of 10 kDa in Epidermoid Carcinoma A431," Journal of Investigative Dermatology, vol. 119, No. 5, pp. 1080-1089, (2002).
Pfister, R., et al., "Natriuretic peptides BNP and NT-pro-BNO: established laboratory markers in clinical practice or just perspectives?" Clinica Chimica Acta, Amsterdam, NL: vol. 349, No. 1-2, pp. 25-38, (2004).
Berger et al., "Proteinase 3, the Major Autoantigen of Wegener's Granulomatosis, Enhances IL-8 Production by Endothelial Cells In Vitro[1]", J. Am. Soc. Nephrol., 1996, 7(5):694-701.
Diavant NT-proBNP, Diagnostic Test of Roche. 1 page. (German Language Translation).
Grosser et al., "Biological basis for the cardiovascular consequence of COX-2 inhibition: therapeutic challenges and opportunities", The Journal of Clinical Investigation, 2006, 116(1):4-15.
Guerreiro et al., "Toxicogenomics in Drug Development", Toxicologic Pathology, 2003, 31:471-479.
Guher et al., "Cytokines and chemokines in neuro-Behçet's disease compared to multiple sclerosis and other neurological diseases", Journal of Neuroimmunology, 2003, 145(1-2):127-134, (Abstract).
International Search Report for International Application PCT/IB2006/000533, provided by the International Searching Authority, mailed Oct. 13, 2006.
Kano et al., "Cellular and Molecular Dynamics in Exercise-Induced Urticarial Vasculitis Lesions", Archives of Dermatology, 1998, 134:62-67, Date of Access: Jun. 1, 2016, http://archderm.jamanetwork.com/article.aspx?articleid=188563.
Kearney et al., "Do selective cyclo-oxygenase-2 inhibitors and traditional non-steroidal anti-inflammatory drugs increase the risk of atherothrombosis? Meta-analysis of randomised trials", BMJ Online First, 2006.
Palop-Larrea et al., "Leukocytoclastic vasculitis related to rofecoxib", Annals of Pharmacotherapy, 2003, 37:1731-1732.
Sari et al., Interferon alpha-Inducible Protein 27 (IF127) is Upregulated in Psoriatic Skin and Certain Epithelial Cancers, J. Invest. Dermatol., 2004, 122(3):717-721.

(Continued)

*Primary Examiner* — Antonio Galisteo Gonzalez
(74) *Attorney, Agent, or Firm* — Hoxie & Associates LLC

(57) ABSTRACT

The present invention is directed to methods for detecting the presence of minimal or early vasculitis or other vasculopathies induced by a cox-2 inhibitor in a subject to whom a cox-2 inhibitor has been administered, selection of cox-2 inhibitory compounds, use of a cox-2 inhibitory compounds in the manufacture of anti-inflammatory medicaments, and vaccination strategies.

3 Claims, 8 Drawing Sheets

(56) References Cited

OTHER PUBLICATIONS

Schneider et al., "Fatal allergic vasculitis associated with celecoxib", The Lancet, 2002, 359(9309):852-853, (Abstract).
Terai et al, "Dramatic decrease of circulating levels of monocyte chemoattractant protein-1 in Kawasaki disease after gamma globulin treatment", Journal of Leukocyte Biology, 1999, 65:566-572.
United States Food and Drug Administration, "Drugs: Information for Healthcare Professional Celecoxib", Apr. 7, 2005. 2 pages.
Wright et al., "Differential regulation of prostaglandin E biosynthesis by interferon-γ in colonic epithelial cells", British Journal of Pharmacology, 2004, 141(7):1091-1097.

PCA analysis for selected genes.
Data from 6 cardiovascular tissues. The Vioxx-treated Monkey #A60055(circled) exhibited distinct expression pattern.

Specific mRNA expression pattern in the Monkey #A60055

The pattern consisted of transcripts for MHC class I, II and class I, non classical molecules, their receptors (TcRs and NK receptors) and chemokines (CXCL9, -10, -11, MCP-1). Overall signature indicating strong INF pathway activation together with IL1/TNF, and coagulation and complement pathways alteration Minimal Focal Vasculatis in the Vioxx®-
treated animal only.
(A) Iliac vein from vehicle treated animal.
(B) Histopathology findings of endothelial cell
(EC) necrosis, fibrin leukocyte adhesion to EC
surface, fibrinoid degeneration of the media,
Medial leukocytes infiltration in iliac vein of the
monkey #A60055.

Marked increase in the transcript expression of CXCL10 (IP10) in several cardiovascular tissues from the Vioxx®-treated monkey #A60055.

Protein profiling in serum and plasma using RBM® multiplex assay.
The monkey #A60055 exhibit a specific protein expression profile: soluble MHC molecules, b2-m, other chemokines, cytokines (INFγ, CXCL10, MCP-1, IL18, TNF RII, IL1b), and soluble VCAM-1.

ELISA confirmation of CXCL10 (IP10) protein level in monkey serum samples.

The Vioxx®-treated monkey #A60055 exhibits the highest level of CXCL10 protein expression.

ELISA confirmation of CXCL10 (IP10) protein level in monkey serum samples.
The Vioxx®-treated monkey #A60055 exhibits the highest level of INFγ protein expression.

Localisation of PD-ECGF1 protein at the site of vascular lesion.

BIOMARKERS FOR CARDIOVASCULAR SIDE-EFFECTS INDUCED BY COX-2 INHIBITORY COMPOUNDS

CROSS REFERENCE TO RELATED APPLICATIONS

This application is a divisional application of U.S. application Ser. No.: 12/293,652, filed Nov. 25, 2009. The 12/293,652 application claims priority to International Application Serial No. PCT/IB2006/000533, filed Mar. 10, 2006, which claims priority to U.S. Provisional Application Ser. No.: 60/661,192, filed on Mar. 11, 2005, each of which are incorporated herein by reference.

FIELD OF THE INVENTION

The invention relates generally to the in vivo testing of the efficacy of a compound or composition, and particularly to the testing and biologically functionalizing of cox-2 inhibitory compounds (coxibs) by activity in vivo.

BACKGROUND OF THE INVENTION

Use of cox-2 specific inhibitory compounds (coxibs) and some NSAIDs has been associated with an increased risk of cardiovascular events in human including deep venous thrombosis, myocardial infarction, stroke, and sudden death. The current hypothesis is that some of anti-inflammatory compounds inhibit PGI2 synthesis but not TxA synthesis, altering the homeostatic balance towards the pro-coagulative/pro-trombotic pathways. Fitzgerald G A. *N Engl J Med.* 351(17):1709-11 (Oct. 21, 2004). It has been reported that some of anti-inflammatory compounds, mainly cox-2 inhibitors, inhibit PGI2 synthesis only, resulting in altered homeostatic balance towards the pro-coagulative pathways which in rare cases might lead to the serious cardiovascular side effects in human. Furberg C D, Psaty B M, FitzGerald G A. *Circulation.* 111(3):249 (Jan. 25, 2005).

There continues to be a need in the art for additional information about the cardiovascular side effects of the use of cox-2 specific inhibitory compounds.

SUMMARY OF THE INVENTION

A 2-week analysis in cynomolgus monkeys (*Macaca fascicularis*) treated with the coxibs COX189 (Lumiracoxib®, Novartis), rofecoxib (Vioxx®, Merck), and celecoxib (Celebrex®, Pharmacia/Pfizer), and with the nonselective NSAID, diclofenac (Voltaren®, Novartis) showed that the Vioxx®—treated animals exhibit a specific mRNA expression pattern which shows the presence of an intravascular procoagulative/prothrombotic state particularly in venous vessels of a Vioxx®—treated monkey. The specific genomic pattern includes gene expression changes involved in blood and endothelial cell (EC) activation, interaction of blood cells with EC, activation of INFγ pathway, and release of pro-inflammatory cytokines and chemo-attractants. These data together with biochemical and histopathological findings indicate that Vioxx® induces or worsens the pro-coagulative/pro-thombotic changes, along with the activation of INFγ pathways triggered most probably by a endothelium tropic viral infection (e.g., cytomegalovirus (CMV)) and/or other vascular INFγ/TNF inducing situations (e.g., autoimmune vascular disorders).

The overall genomic findings show that Cox-2/PGE2 inhibition results in strong and uncontrolled induction of INFγ regulated chemo-attractants, adhesion molecules, and proinflammatory/pro-coagulative molecules which might lead to or increase the risk of cardiovascular adverse events. Histopathological results confirmed the genomic findings showing that the specific genomic pattern is an early signature of vasculitis and is observed only in the animal treated with Vioxx®.

Accordingly, the invention provides biomarkers (in the form of genomic information and serum or plasma proteins) for minimal and early vasculitis or other vasculopathies. In addition, the invention provides biomarkers for predicting potential Vioxx®-induced cardiovascular adverse effects.

Identification of biomarkers advantageously allows safe use of cox-2 inhibitory compounds in clinics and selection of cox-2 inhibitory follow-up compounds without cardiovascular toxicity. Indeed, the expression of several genes increased in the vessels of the Vioxx®-treated animal encode for secreted proteins, e.g., chemokine (CXC motif) ligand 10 (CXCL10) and other cytokines, which can be measured in peripheral samples such as blood or urine. Clinical screening of patients prior to, or during administration of Cox-2 inhibitory therapies should increase their safety profile.

Monitoring of early changes is predictive of cardiovascular adverse effects in patients treated with compounds exhibiting cox-2 inhibition or increasing the production of molecules induced by interferons, by virus infections, or autoimmune disorders resulting in pro-coagulative/pro-thrombotic/endothelium changes. These compounds include mainly cox-2 inhibitors, classical NSAIDs, other anti-inflammatory compounds and direct PGE2, cAMP and PKA inhibitors.

In one aspect of the invention, the data of the present invention identifies another pathway than the PGI2 synthesis pathway that may be one of the main triggering factors leading to the observed adverse cardiovascular events in human. Alteration in this pathway can be easily monitored in preclinical and clinical studies to avoid such cardiovascular side effects upon cox-2 and/or NSAIDs treatments. Biomarkers or the gene signature identified in this invention can also be used to monitor viral infection/INFγ pathway activation and some vasculopathies in diverse human diseases including several autoimmune and neurodegenerative disorders with or without anti-inflammatory and immuno-suppressive treatments. Some of the biomarkers can be used for selection of compounds without potential cardiovascular side-effects.

DETAILED DESCRIPTION OF THE INVENTION

Figure 1:
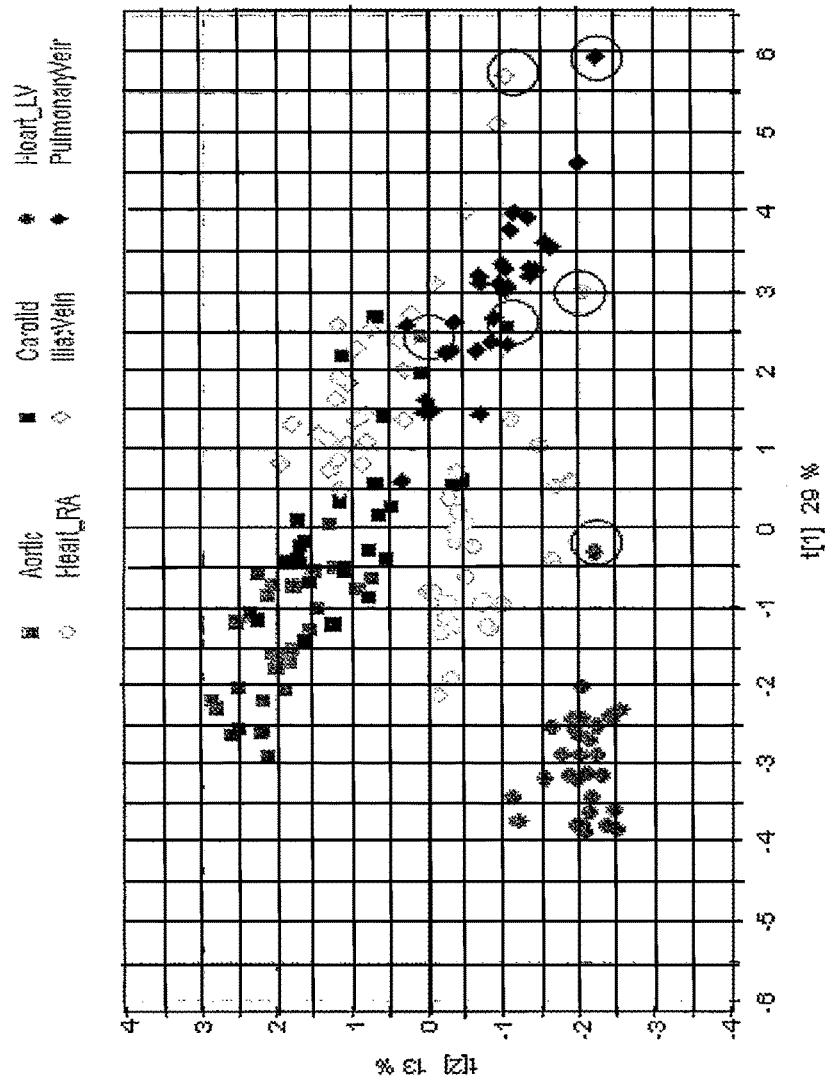
FIG. 1. Principal Component Analysis (PCA) of genomic data from six cardiovascular tissues: iliac vein, pulmonary vein, aorta, carotid artery, heart ventricle, and heart atrium. Only genes encoding for MHC molecules and their receptors were included for PCA analysis. The Vioxx®-treated monkey #A60055 (circled) exhibited distinct expression pattern.

Introduction and overview. The classical discovery process in the pharmaceutical industry is based on targets (enzymes, receptors, cellular assays, animal and disease models, etc.). Chemicals or biological products are tested, in a high-throughput mode, on a battery of pre-selected different targets. The weakness of the classical approach are the "artificially disconnected" in vitro target models compared to the tightly interconnected and interdependent relationship of the different targets in a whole organism and the fact that biological activity on all non selected targets is missed.

By contrast, the invention is a "non pre-conceived hypothesis" discovery process to rapidly identify and analyze the biological activity of new products in the whole organism, multi-organs and whole transcriptome. All physiological interactions between the different organs or tissues are present and any cellular pathway or any potential targets could potentially be analyzed in a non artificial system.

The data of the invention derived from this comparative multi-organ genomics analysis, coupled with extensive clinical, biochemical and histopathological data, identified a new pathway which may play the major role in the cardiovascular events observed in human treated with cox-2 inhibitors. The mRNA expression changes have been analyzed in several tissue samples from Macaca fascicularis following treatment with the Cox-2 specific inhibitors COX189 (Lumiracoxib®, Novartis), Rofecoxib (Vioxx®, Merck), and Celecoxib (Celebrex®, Pharmacia/Pfizer), and with the nonselective NSAID, Diclofenac (Voltaren®, Novartis).

Administration of compounds. A two-week oral-gavage treatment with the Cox-2 specific inhibitor COX189 (Lumiracoxib®, Novartis) in comparison with rofecoxib (Vioxx®, Merck), and celecoxib (Celebrex®, Pharmacia/Pfizer), and with the nonselective NSAID, diclofenac (Voltaren®, Novartis) was performed. All test items were administered to monkeys at doses higher than those used in patients to analyse mRNA expression changes in terms of mechanisms of drug actions and also potential cardiovascular toxic effects. The test items were administered daily at doses of 100 mg/kg/day, except Vioxx® which was administered at 50 mg/kg/day.

In one embodiment of the invention, the test animal is a vertebrate. In a particular embodiment, the vertebrate is a mammal. In a more particular embodiment, the mammal is a primate, such as a cynomolgus monkey (*Macaca fascicularis*). As used herein, the administration of an agent or drug to a subject includes self-administration and the administration by another.

In more particular embodiments, the "treatment group" of animals received a substance (test item, compound, drug) in a vehicle compound suitable for administration of the substance or the combination of substances, while the "control" (or "baseline") group should receive the vehicle compound only. During the treatment period biological specimen such as tissue pieces (e.g. obtained by biopsy), or body fluids, such as blood, plasma, serum, urine, or saliva, can be sampled. At the end of the treatment time all animals of all groups can be sacrificed and biological specimen such as whole organs or pieces thereof can be sampled. All sampled specimen can be stored as known in the art for further analysis that include, but are not limited to, RT-PCR, Northern blotting, in-situ hybridization, gene expression profiling with microarrays.

In one embodiment, the invention begins with differentially expressed transcripts in different cardiovascular tissues and proteins in plasma between normal monkeys and cox-2 inhibitory compounds/drugs-treated monkeys with regard to the identification and validation of potential targets and the identification of biomarkers for cardiovascular side effects.

Gene expression profiles. After a period of time (e.g., four weeks) of compound/drug administration, the treated animals are necropsied. 120 tissues are dissected and rapidly snap-frozen for genomics analysis. Organ samples are isolated for histopathological examinations and for gene expression localizations, such as by in situ hybridization.

In more particular embodiments, the methods of detecting the level of expression of mRNA are well-known in the art and include, but are not limited to, reverse transcription PCR, real time quantitative PCR, Northern blotting and other hybridization methods. A particularly useful method for detecting the level of mRNA transcripts obtained from a plurality of genes involves hybridization of labelled mRNA to an ordered array of oligonucleotides. Such a method allows the level of transcription of a plurality of these genes to be determined simultaneously to generate gene expression profiles or patterns.

As used herein, a gene expression profile is diagnostic when the increased or decreased gene expression is an increase or decrease over the baseline gene expression following administration of a compound.

In one embodiment, the technique for detecting gene expression includes the use of a gene chip. The construction and use of gene chips are well known in the art. See, U.S. Pat. Nos. 5,202,231; 5,445,934; 5,525,464; 5,695,940; 5,744,305; 5,795,716 and 5,800,992. See also, Johnston, M. *Curr Biol* 8:R171-174 (1998); Iyer V R et al., *Science* 283:83-87 (1999) and Elias P, "New human genome 'chip' is a revolution in the offing" *Los Angeles Daily News* (Oct. 3, 2003).

Additional procedures that can be used in the methods of the invention are described in PCT/EP2004/012572, "USE OF ORGANIC COMPOUND", filed Nov. 11, 2004, incorporated herein by reference).

Gene expression profiles have been generated using the Affymetrix microarray technology. (i) RNA extraction and purification: Briefly, total RNA was obtained by acid guanidinium thiocyanate-phenol-chloroform extraction (Trizol®, Invitrogen Life Technologies, San Diego, Calif.) from each frozen tissue section and the total RNA was then purified on an affinity resin (Rneasy®, Qiagen) according to the manufacturer's instructions. Total RNA was quantified by the absorbance at $\lambda=260$ nm ($A_{260\ nm}$) and the purity was estimated by the ratio $A_{260\ nm}/A_{280\ nm}$. Integrity of the RNA molecules was confirmed by non-denaturing agarose gel electrophoresis. RNA was stored at −80° C. until analysis. One part of each individual RNA sample was kept for the analysis of critical genes by means of Real-time PCR. (ii) GeneChip® experiment: All GeneChip® experiments were conducted in the Genomics Factory EU following recommendations by the manufacturer of the GeneChip® system (Affymetrix, *Expression Analysis Technical Manual* (Affymetrix, Santa Clara, Calif., 2005). Human U133A genome arrays were used for transcript expression analysis. Double stranded cDNA was synthesized with a starting amount of approximately 5 μg full-length total RNA using the Superscript Choice System (Invitrogen Life Technologies) in the presence of a T7-(dT) 24 DNA oligonucleotide primer. Following synthesis, the cDNA was purified by phenol/chloroform/isoamyl alcohol extraction and ethanol precipitation. The purified cDNA was then transcribed in vitro using the BioArray® High Yield RNA Transcript Labeling Kit (ENZO) in the presence of biotinylated ribonucleotides form biotin labelled cRNA. The labelled cRNA was then purified on an affinity resin (Rneasy, Qiagen), quantified and fragmented. An amount of approximately 10 μg labelled cRNA was hybridized for approximately 16 hours at 45° C. to an expression probe array. The array was then washed and stained twice with streptavidin-phycoerythrin (Molecular Probes) using the GeneChip Fluidics Workstation 400 (Affymetrix). The array was then scanned twice using a confocal laser scanner (GeneArray Scanner®, Agilent) resulting in one scanned image. This resulting ".dat-file" was processed using the MASS program (Affymetrix) into a ".cel-file". The ".cel file" was then transferred to tan Affymetrix GeneChip Laboratory Information Management System (LIMS) database, which is connected to a UNIX Sun Solaris server through a network filing system that allows for the average intensities for all probes cells (CEL file) to be downloaded into an Oracle database (NPGN). Raw data was converted to expression levels using a "target intensity" of 100. The numerical values displayed are weighted averages of the signal intensities of the probe-pairs comprised in a probe-set for a given transcript sequence (AvgDiff value). The data were checked for quality and loaded in the GeneSpring® software versions 5.0 (Silicon Genetics, Calif., US) for statistical analysis.

Quality control analysis of transcriptome data: The following quality measures were analysed for each sample: Scaling factor, background, percent present calls, AFFX-GAPDH 3': AFFX-GAPDH 5'-ratio, AFFX-GAPDH 3' variance, AFFX-Beta-actin 3': AFFX-Beta-actin 5'-ratio. Biological outliers and tissue contamination were identified using NPGN-database Gene Expression Tools by comparing the average signal intensity per probe set per treatment group to the signal intensity in each sample. Attention was paid to the homogeneity of the data. Average and standard deviation of the background noise level determined the raw data restriction value used in the consequent analysis.

Principal component analysis of transcriptome data: Using SIMCA 10.5 software (Umetrics Inc, Kinnelon N.J., USA), Principal Component Analysis (PCA) was performed on all data generated by the microarrays or on, genes present at least in 2 out of 4 samples in at least 1 group to determine general expression differences/similarities among the samples and identify potential biological or technical outliers. A projection was made on the first two or three principal components for each tissue. Here, the differences between samples represent differences in the level of expression or in the correlation structure of the genes used for the PCA model.

The information was further refined by the use of complementary techniques. In situ hybridization, for example, can indicate precisely which cell type inside an organ is specifically expressing a given gene. This technique based on the detection of RNA is independent of the availability of an antibody. Quantitative PCR has also been used to confirm expression levels of particular genes of interest.

To obtain biomarkers predicting cardiovascular adverse effect of tested compounds/drugs, expression levels of proteins have been analysed in cynomolgus monkey serum and plasma from the present analysis using human Multi-Analyte Profile (MAP) Technology. Human MAP could be used to measure protein levels of more than 80 antigens in monkey serum and plasma (Rules-Based Medicine Inc (RBM®), Austin, Tex. USA).

The following EXAMPLE is presented in order to more fully illustrate the preferred embodiments of the invention. This EXAMPLE should in no way be construed as limiting the scope of the invention, as defined by the appended claims.

EXAMPLE

Identification of Specific Genomics Signature in Vioxx®-Treated Monkey(s)

Overall genomics data obtained for 16 tissues from all monkey groups showed that the Vioxx®-treated animals exhibit a specific pattern of gene expression. This pattern includes significant increases (ANOVA, $p<0.05$) in the expression of MHC class I classical and non-classical molecules, MHC class II molecules and their respective receptors such as TcRs and Immunoglobulin-like molecules.

Analysis of genomic data from several cardiovascular tissues by Principle Component Analysis (PCA) on the selected genes composed of MHC molecules identified a biological outlier (Animal no: A60055, circled in the FIG. 1) within the Vioxx®-treated group.

Figure 2:
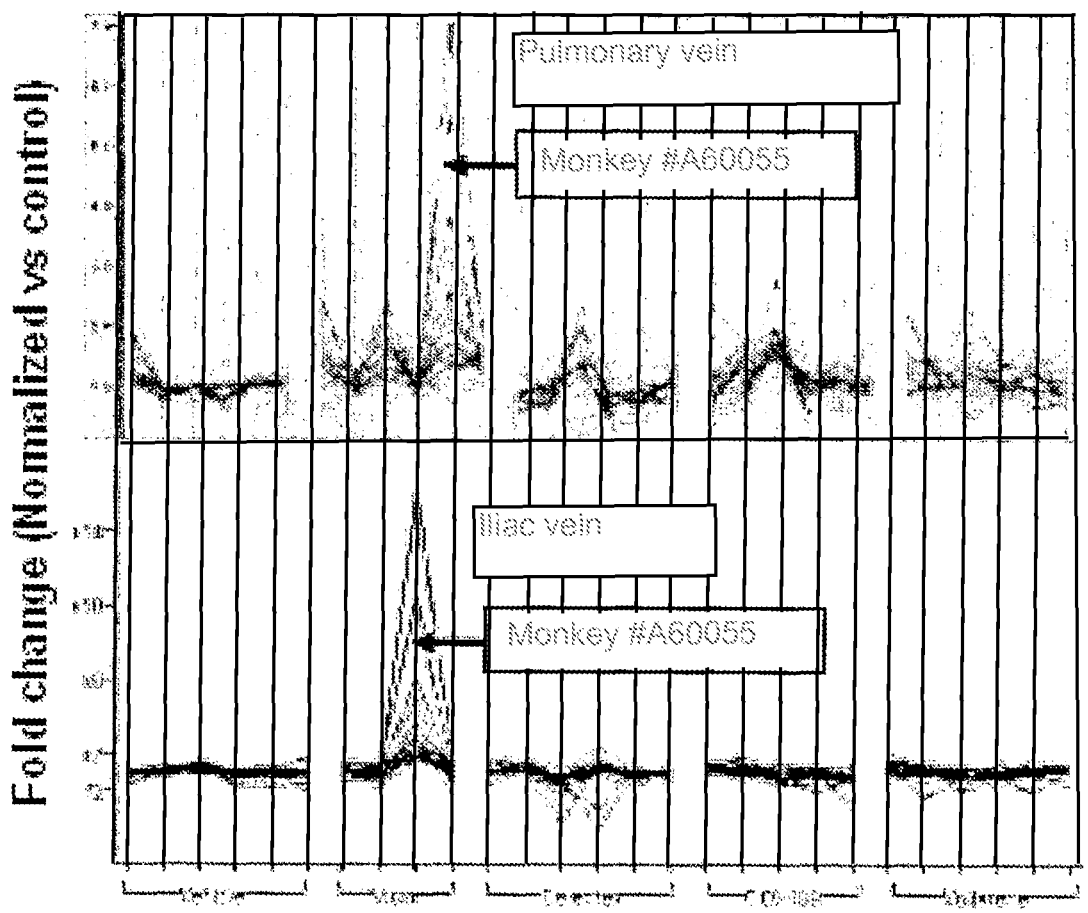
FIG. 2. Specific genomics expression pattern in Vioxx®-treated monkey #A60055. The pattern consisted of transcripts for MHC class I, II & class I, non classical molecules, their receptors (TcRs and NK receptors), chemokines (CXCL9, -10, -11, MCP-1). Overall signature indicating strong INF pathway activation together with IL1/TNF and coagulation and complement pathways alteration.

Further analysis of all genomic data by PLS-DA provided a list of the most discriminate genes between the animal A60055 and the rest of the animals from Vioxx®, Celebrex®, Cox189 (Novartis), diclofenac and vehicle treated groups (TABLE 1, FIG. 2). The specific gene pattern included mainly interferon inducible genes encoding for Toll like receptors (TLRs), classical and non-classical MHC class I, MHC class II, their respective receptors/ligands such as TcRs and NK receptors, several chemokines such as CXCL10, CCL2, an extensive list of INFγ pathways signalling genes such as Jak1, Stat1, and some IL1/TNF pathway related molecules. In addition, there was strong and significant increases in the expression of coagulation pathways related molecules such as PD-ECGF, coagulation factor II (thrombin) receptor-like 1, Factor 13 A1, several adhesion molecules such as VCAM and ICAM, and a number of genes belonging to the complement activation and other pathways innate immunity pathways. This genomic expression pattern predominant in the vessels of the Vioxx®-treated monkey (#A60055) indicated development of a potential vasculopathy/vasculitis with strong activation of INFγ pathway suggestively induced by an endothelium tropic infection or reactivation of a vascular autoimmune disorder.

Figure 3:
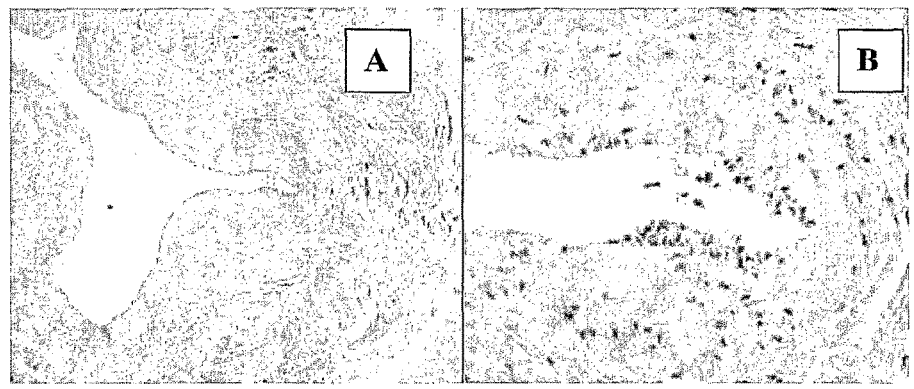
FIG. 3. Histopathological evaluation of samples from different tissues confirms the genomic data showing focal vascular necrosis in the veins of Vioxx®-treated animal #A60055 only. The main findings consisted of EC necrosis, leucocytes/fibrin adhesion to EC surface, fibrinoid degeneration of the media and medial leukocyte infiltration. (A) Iliac vein from vehicle treated animal. (B) Histopathology findings of endothelial cell (EC) necrosis, fibrin leukocyte adhesion to EC surface, fibrinoid degeneration of the media, medial leukocytes infiltration in iliac vein of the monkey #A60055.

Interestingly, histopathological evaluation of all tissues showed clear sign of vasculitis in veins only of the Vioxx®-treated animal A60055 (FIG. 3). Thus the specific expression pattern should be a specific genomics signature of minimal vasculitis (see below).

Figure 4:
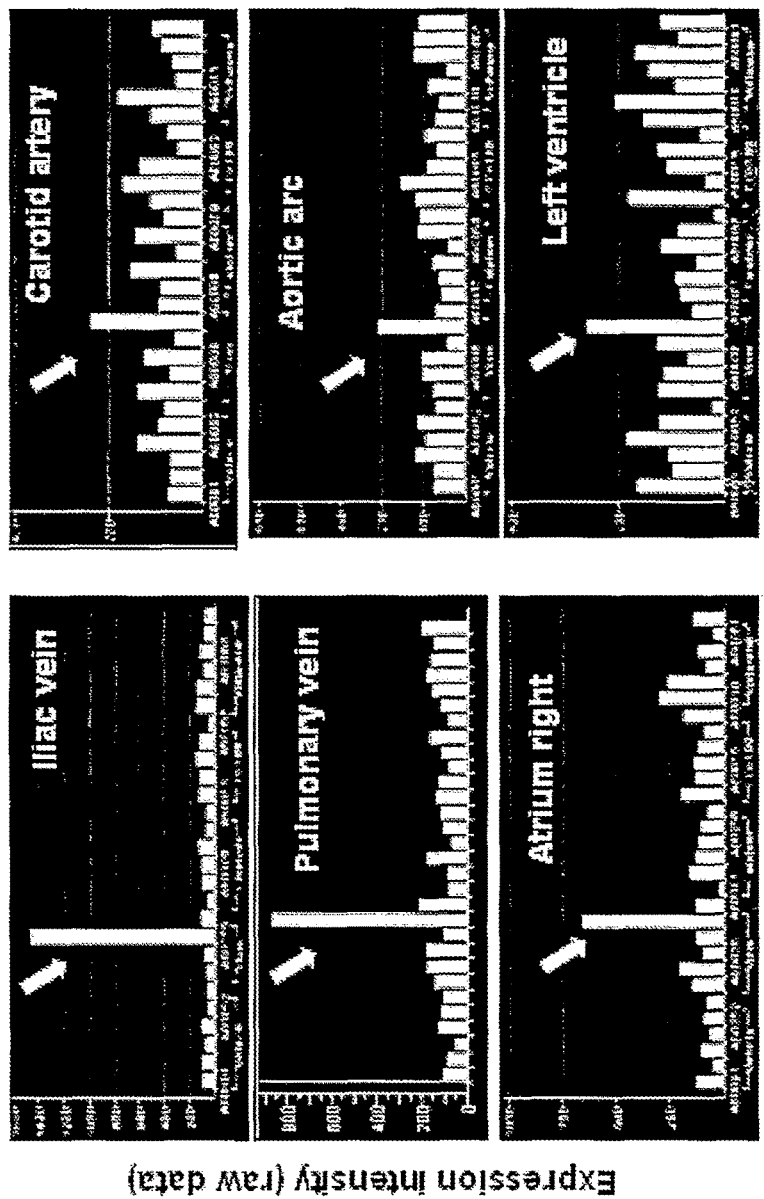
FIG. 4. Strong increase of CXCL10 in veins followed by arteries and heart samples from the Vioxx®-treated monkey #A60055 (indicated by an arrow) only.

The role of Vioxx®-induced cox-2 inhibition in the observed genomic and histopathological findings provide a potential link to the increased risks of cardiovascular side effects occurring in patients treated with Vioxx®: The majority of the observed gene expression changes have been known to be directly involved in the pathogenesis of diverse cardiovascular diseases including atherosclerosis, CAD, thrombosis, autoimmune and neurodegenerative diseases. Among the INFγ inducible gene expression changes, the most striking increase was observed for CXCL10 and other chemokines, e.g., CXCL-9, -11 and MCP-1 (CCL-2) (FIG. 4 and TABLE 1).

TABLE 1

The most discriminant genes for Vioxx animal #A60055 and corresponding genomics expression data from iliac vein samples of monkeys treated with vehicle, Vioxx®, Celebrex®, Cox189 (Novartis), and diclofenac. These results indicated potential vasculopathies in the animal A60055, probably induced by an unknown virus infection together with an exaggerated host immune response against vascular endothelium.

| Systematic Name | SYMBOL | GENENAME | Control Avg | SD | Vioxx A60055 | Vioxx without A60055 | Celebrex | Cox189 | Voltaren |
|---|---|---|---|---|---|---|---|---|---|
| | | | | | | Avg fold changes vs control | | | |
| 216598_s_at | CCL2 | chemokine (C-C motif) ligand 2 | 6 | 1 | 150.9 | 1.0 | 2.3 | 1.6 | 9.0 |
| 202411_at | IFI27 | interferon, alpha-inducible protein 27 | 20 | 12 | 20.8 | 3.8 | 3.3 | 4.2 | 5.6 |
| 204533_at | CXCL10 | chemokine (C—X—C motif) ligand 10 | 74 | 20 | 19.8 | 1.1 | 1.1 | 1.4 | 1.3 |
| 209969_s_at | STAT1 | signal transducer and activator of transcription 1, 91 kDa | 50 | 16 | 13.5 | 1.7 | 2.7 | 1.4 | 2.3 |
| 212998_x_at | HLA-DQB2 | major histocompatibility complex, class II, DQ beta 2 | 252 | 86 | 10.8 | 1.2 | 1.9 | 1.4 | 2.2 |
| 210163_at | CXCL11 | chemokine (C—X—C motif) ligand 11 | 4 | 5 | 9.7 | 1.5 | 3.7 | 2.6 | 2.1 |
| 203915_at | CXCL9 | chemokine (C—X—C motif) ligand 9 | 64 | 21 | 9.3 | 1.6 | 1.4 | 1.7 | 1.3 |
| 214038_at | CCL8 | chemokine (C-C motif) ligand 8 | 19 | 13 | 8.8 | 1.8 | 1.3 | 1.7 | 1.8 |
| 214453_s_at | IFI44 | interferon-induced protein 44 | 141 | 24 | 8.2 | 2.5 | 1.3 | 2.0 | 1.7 |
| 212671_s_at | HLA-DQA1 | major histocompatibility complex, class II, DQ alpha 1 | 445 | 167 | 8.2 | 1.0 | 2.1 | 1.6 | 1.2 |
| 211654_x_at | HLA-DQB1 | major histocompatibility complex, class II, DQ beta 1 | 544 | 143 | 7.7 | 1.0 | 2.0 | 1.8 | 1.6 |
| AFFX-HU-MISGF3A/M97935_MB_at | STAT1 | signal transducer and activator of transcription 1, 91 kDa | 109 | 25 | 7.1 | 1.5 | 1.2 | 1.9 | 1.1 |
| 213797_at | cig5 | viperin | 25 | 17 | 7.1 | 1.4 | 1.3 | 1.8 | 2.1 |
| 211122_s_at | CXCL11 | chemokine (C—X—C motif) ligand 11 | 10 | 9 | 6.6 | 1.0 | 1.6 | 2.3 | 2.0 |
| 210029_at | INDO | indoleamine-pyrrole 2,3 dioxygenase | 53 | 16 | 6.5 | 1.1 | 1.6 | 1.2 | 1.4 |
| 214567_s_at | XCL1 | chemokine (C motif) ligand 1 | 13 | 12 | 5.4 | 1.1 | 3.5 | 1.3 | 0.5 |
| AFFX-HUMISGF3A/M97935_MA_at | STAT1 | signal transducer and activator of transcription 1, 91 kDa | 99 | 7 | 5.3 | 1.3 | 1.3 | 1.2 | 1.0 |
| 203153_at | IFIT1 | interferon-induced protein with tetratricopeptide repeats 1 | 100 | 35 | 5.0 | 1.5 | 0.8 | 1.1 | 1.0 |
| 217502_at | IFIT2 | interferon-induced protein with tetratricopeptide repeats 2 | 168 | 62 | 4.7 | 1.3 | 1.1 | 1.4 | 0.8 |
| 205483_s_at | G1P2 | interferon, alpha-inducible protein (clone IFI-15K) | 27 | 13 | 4.5 | 3.3 | 1.4 | 1.5 | 2.1 |
| 206366_x_at | XCL1 | chemokine (C motif) ligand 1 | 33 | 15 | 4.3 | 1.5 | 2.0 | 1.7 | 1.8 |
| AFFX-HU-MISGF3A/M97935_5_at | STAT1 | signal transducer and activator of transcription 1, 91 kDa | 25 | 16 | 4.3 | 1.3 | 0.9 | 1.6 | 1.0 |
| 209823_x_at | HLA-DQB1 | major histocompatibility complex, class II, DQ beta 1 | 233 | 102 | 4.3 | 0.9 | 2.0 | 1.0 | 1.3 |
| 204820_s_at | BTN3A3 | butyrophilin, subfamily 3, member A3 | 324 | 48 | 4.1 | 1.6 | 1.3 | 1.1 | 1.3 |
| 203868_s_at | VCAM1 | vascular cell adhesion molecule 1 | 285 | 164 | 4.1 | 0.8 | 1.9 | 0.9 | 1.4 |
| 211656_x_at | HLA-DQB1 | major histocompatibility complex, class II, DQ beta 1 | 421 | 132 | 4.1 | 1.0 | 1.6 | 1.3 | 1.2 |
| 207485_x_at | BTN3A1 | butyrophilin, subfamily 3, member A1 | 55 | 28 | 4.0 | 2.0 | 1.7 | 2.1 | 1.1 |
| 202531_at | IRF1 | interferon regulatory factor 1 | 290 | 49 | 3.9 | 0.8 | 1.1 | 1.3 | 1.1 |
| 214234_s_at | CYP3A5 | cytochrome P450, family 3, subfamily A, polypeptide 5 | 28 | 11 | 3.9 | 0.9 | 1.3 | 1.3 | 1.2 |
| 205114_s_at | CCL3 | chemokine (C-C motif) ligand 3 | 21 | 12 | 3.8 | 1.4 | 1.3 | 0.9 | 1.4 |
| 208451_s_at | C4A | complement component 4A | 220 | 121 | 3.8 | 1.1 | 1.6 | 0.9 | 2.4 |
| 208747_s_at | C1S | complement component 1, s subcomponent | 1786 | 602 | 3.6 | 1.3 | 1.0 | 1.0 | 1.7 |
| 205898_at | CX3CR1 | chemokine (C—X3—C motif) receptor 1 | 86 | 36 | 3.6 | 1.0 | 1.1 | 1.2 | 1.6 |
| 208071_s_at | LAIR1 | leukocyte-associated Ig-like receptor 1 | 37 | 25 | 3.5 | 0.5 | 3.6 | 1.1 | 0.8 |
| 208436_s_at | IRF7 | interferon regulatory factor 7 | 24 | 11 | 3.4 | 1.6 | 2.1 | 1.6 | 1.2 |

TABLE 1-continued

The most discriminant genes for Vioxx animal #A60055 and corresponding genomics expression data from iliac vein samples of monkeys treated with vehicle, Vioxx ®, Celebrex ®, Cox189 (Novartis), and diclofenac. These results indicated potential vasculopathies in the animal A60055, probably induced by an unknown virus infection together with an exaggerated host immune response against vascular endothelium.

| Systematic Name | SYMBOL | GENENAME | Control Avg | Control SD | Vioxx A60055 | Vioxx without A60055 | Celebrex | Cox189 | Voltaren |
|---|---|---|---|---|---|---|---|---|---|
| | | | | | | Avg fold changes vs control | | | |
| 204858_s_at | ECGF1 | endothelial cell growth factor 1 (platelet-derived) | 78 | 30 | 3.3 | 1.9 | 1.1 | 1.7 | 1.4 |
| 209785_s_at | PLA2G4C | phospholipase A2, group IVC (cytosolic, calcium-independent) | 46 | 17 | 3.3 | 1.2 | 1.4 | 1.4 | 1.0 |
| 203052_at | C2 | complement component 2 | 205 | 16 | 3.3 | 0.9 | 1.1 | 1.1 | 1.2 |
| 204821_at | BTN3A3 | butyrophilin, subfamily 3, member A3 | 40 | 15 | 3.3 | 1.7 | 1.6 | 1.5 | 1.5 |
| 213095_x_at | AIF1 | allograft inflammatory factor 1 | 78 | 62 | 3.2 | 0.6 | 2.0 | 0.5 | 1.5 |
| 210164_at | GZMB | granzyme B (granzyme 2, cytotoxic T-lymphocyte-associated serine esterase 1) | 19 | 10 | 3.2 | 1.6 | 0.9 | 0.8 | 1.8 |
| 203882_at | ISGF3G | interferon-stimulated transcription factor 3, gamma 48 kDa | 402 | 53 | 3.1 | 1.7 | 1.0 | 1.5 | 1.4 |
| 209901_x_at | AIF1 | allograft inflammatory factor 1 | 111 | 74 | 3.0 | 0.3 | 1.5 | 0.7 | 1.2 |
| 201891_s_at | B2M | beta-2-microglobulin | 318 | 105 | 3.0 | 1.4 | 1.3 | 1.0 | 1.4 |
| 210072_at | CCL19 | chemokine (C-C motif) ligand 19 | 78 | 28 | 3.0 | 1.2 | 2.0 | 1.4 | 1.6 |
| 208893_s_at | DUSP6 | dual specificity phosphatase 6 | 107 | 40 | 3.0 | 1.0 | 1.2 | 0.9 | 1.1 |
| 217478_s_at | HLA-DMA | major histocompatibility complex, class II, DM alpha | 838 | 145 | 2.9 | 1.1 | 1.4 | 1.2 | 1.3 |
| 202705_at | CCNB2 | cyclin B2 | 43 | 14 | 2.9 | 1.4 | 1.2 | 1.4 | 1.3 |
| 215193_x_at | HLA-DRB1 | major histocompatibility complex, class II, DR beta 1 | 1950 | 212 | 2.9 | 1.2 | 1.7 | 1.5 | 1.3 |
| 202687_s_at | TNFSF10 | tumor necrosis factor (ligand) super-family, member 10 | 533 | 141 | 2.9 | 1.2 | 1.3 | 1.2 | 1.2 |
| 1405_i_at | CCL5 | chemokine (C-C motif) ligand 5 | 8 | 7 | 2.8 | 0.5 | 0.9 | 0.9 | 2.2 |
| 209619_at | CD74 | CD74 antigen (invariant polypeptide of major histocompatibility complex, class II antigen-associated) | 922 | 192 | 2.8 | 1.1 | 1.3 | 1.0 | 1.3 |
| 202688_at | TNFSF10 | tumor necrosis factor (ligand) super-family, member 10 | 373 | 102 | 2.8 | 0.9 | 1.3 | 1.2 | 1.1 |
| 211367_s_at | CASP1 | caspase 1, apoptosis-related cysteine protease (interleukin 1, beta, convertase) | 53 | 13 | 2.7 | 1.4 | 1.2 | 1.2 | 1.3 |
| 204674_at | LRMP | lymphoid-restricted membrane protein | 74 | 31 | 2.6 | 1.7 | 3.8 | 1.6 | 1.6 |
| 202436_s_at | CYP1B1 | cytochrome P450, family 1, subfamily B, polypeptide 1 | 171 | 25 | 2.6 | 1.0 | 1.0 | 1.3 | 1.3 |
| 204006_s_at | FCGR3A | Fc fragment of IgG, low affinity IIIa, receptor for (CD16) | 41 | 19 | 2.5 | 0.8 | 1.3 | 1.0 | 1.5 |
| 214630_at | CYP11B1 | cytochrome P450, family 11, subfamily B, polypeptide 1 | 25 | 12 | 2.5 | 0.8 | 1.1 | 1.0 | 0.9 |
| 210225_x_at | LILRB3 | leukocyte immunoglobulin-like receptor, subfamily B (with TM and ITIM domains), member 3 | 98 | 44 | 2.5 | 0.8 | 1.3 | 1.1 | 1.3 |
| 206060_s_at | PTPN22 | protein tyrosine phosphatase, non-receptor type 22 (lymphoid) | 23 | 11 | 2.5 | 1.0 | 2.5 | 1.2 | 0.9 |
| 204116_at | IL2RG | interleukin 2 receptor, gamma (severe combined immunodeficiency) | 188 | 27 | 2.4 | 1.4 | 3.8 | 1.3 | 1.2 |
| 211528_x_at | HLA-A | major histocompatibility complex, class I, A | 3314 | 497 | 2.4 | 1.3 | 1.1 | 1.3 | 1.1 |
| 209813_x_at | | | 39 | 22 | 2.4 | 0.4 | 1.2 | 1.0 | 1.0 |
| 214459_x_at | HLA-C | major histocompatibility complex, class I, C | 4379 | 649 | 2.4 | 1.4 | 1.3 | 1.2 | 1.3 |
| 216920_s_at | TRGC2 | T cell receptor gamma constant 2 | 72 | 13 | 2.4 | 1.0 | 1.6 | 1.1 | 1.2 |
| 211530_x_at | HLA-A | major histocompatibility complex, class I, A | 868 | 214 | 2.3 | 1.8 | 1.5 | 1.6 | 1.6 |
| 208894_at | HLA-DRA | major histocompatibility complex, class II, DR alpha | 2704 | 518 | 2.3 | 1.0 | 1.3 | 1.2 | 1.1 |
| 38241_at | BTN3A3 | butyrophilin, subfamily 3, member A3 | 36 | 8 | 2.3 | 14 | 1.1 | 1.0 | 1.2 |
| 205758_at | CD8A | CD8 antigen, alpha polypeptide (p32) | 41 | 21 | 2.3 | 1.3 | 1.0 | 1.2 | 1.4 |
| 202644_s_at | TNFAIP3 | tumor necrosis factor, alpha-induced protein 3 | 183 | 50 | 2.3 | 1.2 | 1.7 | 1.3 | 1.7 |
| 221875_x_at | HLA-F | major histocompatibility complex, class I, F | 3883 | 622 | 2.3 | 1.2 | 1.0 | 1.2 | 1.0 |
| 209970_x_at | CASP1 | caspase 1, apoptosis-related cysteine protease (interleukin 1, beta, convertase) | 168 | 26 | 2.3 | 1.1 | 1.2 | 1.1 | 1.5 |
| 203020_at | HHL | expressed in hematopoietic cells, heart, liver | 575 | 183 | 2.2 | 1.1 | 1.4 | 1.0 | 0.8 |
| 217362_x_at | HLA-DRB6 | major histocompatibility complex, class II, DR beta 6 (pseudogene) | 641 | 209 | 2.2 | 1.2 | 1.4 | 1.3 | 1.0 |
| 202465_at | PCOLCE | procollagen C-endopeptidase enhancer | 1093 | 451 | 2.2 | 0.5 | 0.7 | 0.8 | 0.3 |
| 204057_at | ICSBP1 | interferon consensus sequence binding protein 1 | 67 | 21 | 2.2 | 1.4 | 1.6 | 1.2 | 1.1 |

TABLE 1-continued

The most discriminant genes for Vioxx animal #A60055 and corresponding genomics expression data from iliac vein samples of monkeys treated with vehicle, Vioxx ®, Celebrex ®, Cox189 (Novartis), and diclofenac. These results indicated potential vasculopathies in the animal A60055, probably induced by an unknown virus infection together with an exaggerated host immune response against vascular endothelium.

| Systematic Name | SYMBOL | GENENAME | Control Avg | Control SD | Vioxx A60055 | Vioxx without A60055 | Celebrex | Cox189 | Voltaren |
|---|---|---|---|---|---|---|---|---|---|
| | | | | | | Avg fold changes vs control | | | |
| 204890_s_at | LCK | lymphocyte-specific protein tyrosine kinase | 42 | 9 | 2.2 | 1.5 | 3.2 | 1.4 | 0.9 |
| 205926_at | IL27RA | interleukin 27 receptor, alpha | 93 | 37 | 2.2 | 1.1 | 1.1 | 1.1 | 1.3 |
| 208200_at | IL1A | interleukin 1, alpha | 14 | 10 | 2.2 | 1.1 | 0.4 | 1.6 | 1.2 |
| 206541_at | KLKB1 | kallikrein B, plasma (Fletcher factor) 1 | 59 | 32 | 2.2 | 1.2 | 1.1 | 1.0 | 1.2 |
| 208791_at | CLU | clusterin (complement lysis inhibitor, SP-40,40, sulfated glycoprotein 2, testosterone-repressed prostate message 2, apolipoprotein J) | 3952 | 905 | 2.2 | 0.9 | 0.8 | 1.0 | 1.0 |
| 201487_at | CTSC | cathepsin C | 333 | 83 | 2.1 | 1.1 | 1.3 | 1.1 | 1.4 |
| 207857_at | LILRB1 | leukocyte immunoglobulin-like receptor, subfamily B (with TM and ITIM domains), member 1 | 30 | 15 | 2.1 | 0.5 | 1.0 | 0.7 | 0.8 |
| 201422_at | IFI30 | interferon, gamma-inducible protein 30 | 176 | 14 | 2.1 | 1.0 | 1.3 | 1.1 | 1.4 |
| 204806_x_at | HLA-F | major histocompatibility complex, class I, F | 3260 | 520 | 2.1 | 1.1 | 1.2 | 1.2 | 1.0 |
| 210982_s_at | HLA-DRA | major histocompatibility complex, class II, DR alpha | 743 | 100 | 2.1 | 1.0 | 1.5 | 1.1 | 1.0 |
| 215485_s_at | ICAM1 | intercellular adhesion molecule 1 (CD54), human rhinovirus receptor | 158 | 30 | 2.1 | 0.9 | 1.1 | 1.0 | 1.1 |
| 211529_x_at | HLA-A | major histocompatibility complex, class I, A | 3620 | 317 | 2.1 | 1.2 | 1.2 | 1.3 | 1.2 |
| 214377_s_at | JAK1 | Janus kinase 1 (a protein tyrosine kinase) | 84 | 12 | 2.1 | 1.3 | 0.9 | 1.1 | 1.1 |
| 202446_s_at | PLSCR1 | phospholipid scramblase 1 | 641 | 187 | 2.1 | 1.2 | 1.1 | 1.0 | 1.5 |
| 201743_at | CD14 | CD14 antigen | 179 | 26 | 2.0 | 0.8 | 1.1 | 0.7 | 1.1 |
| 216526_x_at | HLA-C | major histocompatibility complex, class I, C | 3770 | 1302 | 2.0 | 1.3 | 1.2 | 1.4 | 1.5 |
| 202643_s_at | TNFAIP3 | tumor necrosis factor, alpha-induced protein 3 | 109 | 31 | 2.0 | 0.8 | 1.5 | 1.2 | 1.3 |
| 206429_at | F2RL1 | coagulation factor II (thrombin) receptor-like 1 | 26 | 15 | 2.0 | 2.0 | 1.1 | 1.8 | 1.5 |
| 211144_x_at | TRGC2 | T cell receptor gamma constant 2 | 64 | 16 | 2.0 | 1.3 | 1.2 | 1.3 | 1.0 |
| 209924_at | CCL18 | chemokine (C-C motif) ligand 18 | 23 | 20 | 2.0 | 0.7 | 1.5 | 2.3 | 1.6 |
| 212067_s_at | C1R | complement component 1, r | 654 | 125 | 2.0 | 0.9 | 0.9 | 1.0 | 1.4 |
| 214511_x_at | FCGR1A | Fc fragment of IgG, high affinity Ia, receptor for (CD64) | 101 | 30 | 2.0 | 0.6 | 1.1 | 1.0 | 1.0 |
| 218009_s_at | PRC1 | protein regulator of cytokinesis 1 | 32 | 14 | 2.0 | 0.7 | 1.1 | 1.0 | 0.8 |
| 220040_x_at | HCA127 | hepatocellular carcinoma-associated antigen 127 | 116 | 54 | 2.0 | 0.6 | 1.0 | 0.9 | 0.5 |
| 209365_s_at | ECM1 | extracellular matrix protein 1 | 156 | 44 | 2.0 | 1.3 | 0.9 | 1.0 | 1.1 |
| 210571_s_at | CMAH | cytidine monophosphate-N-acetylneuraminic acid hydroxylase | 88 | 17 | 2.0 | 1.0 | 1.0 | 1.1 | 1.4 |
| 213539_at | CD3D | CD3D antigen, delta polypeptide (TiT3 complex) | 85 | 39 | 1.9 | 2.0 | 3.2 | 1.7 | 1.9 |
| 209312_x_at | HLA-DRB3 | major histocompatibility complex, class II, DR beta 3 | 3990 | 399 | 1.9 | 1.1 | 1.5 | 1.3 | 1.1 |
| 201315_x_at | IFITM2 | interferon induced transmembrane protein 2 (1-8D) | 1055 | 139 | 1.9 | 1.1 | 1.0 | 1.2 | 1.6 |
| 209140_x_at | HLA-B | major histocompatibility complex, class I, B | 8146 | 1478 | 1.9 | 1.1 | 1.1 | 1.2 | 1.2 |
| 210865_at | TNFSF6 | tumor necrosis factor (ligand) super-family, member 6 | 56 | 10 | 1.9 | 1.1 | 1.4 | 1.3 | 1.2 |
| 206360_s_at | SOCS3 | suppressor of cytokine signaling 3 | 95 | 30 | 1.8 | 0.8 | 0.9 | 1.0 | 1.4 |
| 211100_x_at | LILRB1 | leukocyte immunoglobulin-like receptor, subfamily B (with TM and ITIM domains), member 1 | 77 | 18 | 1.8 | 1.3 | 1.4 | 1.0 | 1.2 |
| 203305_at | F13A1 | coagulation factor XIII, A1 polypeptide | 183 | 27 | 1.8 | 0.9 | 0.9 | 1.1 | 1.3 |
| 209541_at | IGF1 | insulin-like growth factor 1 (somatomedin C) | 524 | 255 | 1.8 | 0.9 | 0.9 | 0.9 | 1.2 |
| 215313_x_at | HLA-A | major histocompatibility complex, class I, A | 5166 | 264 | 1.8 | 1.3 | 1.2 | 1.3 | 1.3 |
| 207238_s_at | PTPRC | protein tyrosine phosphatase, receptor type, C | 137 | 75 | 1.8 | 1.3 | 2.5 | 1.1 | 1.3 |
| 210864_x_at | HFE | hemochromatosis | 159 | 24 | 1.8 | 1.2 | 1.1 | 1.3 | 0.9 |
| 219059_s_at | XLKD1 | extracellular link domain containing 1 | 286 | 63 | 1.8 | 1.0 | 1.5 | 1.0 | 1.4 |
| 211911_x_at | HLA-B | major histocompatibility complex, class I, B | 5982 | 585 | 1.8 | 1.4 | 1.2 | 1.3 | 1.2 |
| 206584_at | LY96 | lymphocyte antigen 96 | 75 | 32 | 1.8 | 1.1 | 1.4 | 1.0 | 1.4 |

TABLE 1-continued

The most discriminant genes for Vioxx animal #A60055 and corresponding genomics expression data from iliac vein samples of monkeys treated with vehicle, Vioxx ®, Celebrex ®, Cox189 (Novartis), and diclofenac. These results indicated potential vasculopathies in the animal A60055, probably induced by an unknown virus infection together with an exaggerated host immune response against vascular endothelium.

| Systematic Name | SYMBOL | GENENAME | Control Avg | SD | Vioxx A60055 | Vioxx without A60055 | Celebrex | Cox189 | Voltaren |
|---|---|---|---|---|---|---|---|---|---|
| | | | | | | Avg fold changes vs control | | | |
| 202953_at | C1QB | complement component 1, q subcomponent, beta polypeptide | 227 | 37 | 1.8 | 1.0 | 1.1 | 1.0 | 1.1 |
| 211329_x_at | HFE | hemochromatosis | 127 | 29 | 1.8 | 0.9 | 0.7 | 0.9 | 0.9 |
| 201858_s_at | PRG1 | proteoglycan 1, secretory granule | 1003 | 235 | 1.8 | 0.8 | 1.0 | 0.9 | 1.1 |
| 208729_x_at | HLA-B | major histocompatibility complex, class I, B | 5968 | 985 | 1.8 | 1.2 | 1.1 | 1.3 | 1.2 |
| 211863_x_at | HFE | hemochromatosis | 160 | 23 | 1.8 | 0.8 | 0.9 | 1.3 | 1.0 |
| 205859_at | LY86 | lymphocyte antigen 86 | 126 | 21 | 1.8 | 1.5 | 1.5 | 0.9 | 1.2 |
| 217456_x_at | HLA-E | major histocompatibility complex, class I, E | 1205 | 148 | 1.8 | 1.2 | 1.2 | 1.4 | 1.2 |
| 203028_s_at | CYBA | cytochrome b-245, alpha polypeptide | 173 | 18 | 1.8 | 1.1 | 1.2 | 1.2 | 1.0 |
| 208018_s_at | HCK | hemopoietic cell kinase | 98 | 36 | 1.8 | 1.2 | 1.4 | 1.1 | 1.2 |
| 208812_x_at | HLA-C | major histocompatibility complex, class I, C | 4921 | 1097 | 1.8 | 1.3 | 1.2 | 1.1 | 1.2 |
| 201508_at | IGFBP4 | insulin-like growth factor binding protein 4 | 2272 | 954 | 1.7 | 0.5 | 0.6 | 0.6 | 0.8 |
| 202803_s_at | ITGB2 | integrin, beta 2 (antigen CD18 (p95), lymphocyte function-associated antigen 1; macrophage antigen 1 (mac-1) beta subunit) | 114 | 31 | 1.7 | 0.6 | 1.1 | 1.0 | 1.0 |
| 204908_s_at | BCL3 | B-cell CLL/lymphoma 3 | 119 | 19 | 1.7 | 0.7 | 1.0 | 1.0 | 1.3 |
| 216217_at | PLCL2 | phospholipase C-like 2 | 28 | 8 | 1.7 | 1.0 | 1.0 | 0.9 | 1.0 |
| 205270_s_at | LCP2 | lymphocyte cytosolic protein 2 | 73 | 18 | 1.7 | 0.9 | 1.9 | 1.2 | 1.2 |
| 210754_s_at | LYN | v-yes-1 Yamaguchi sarcoma viral related oncogene homolog | 255 | 48 | 1.7 | 1.0 | 1.5 | 0.8 | 1.1 |
| 203332_s_at | INPP5D | inositol polyphosphate-5-phosphatase, 145 kDa | 153 | 32 | 1.7 | 1.2 | 1.6 | 1.2 | 1.2 |
| 218232_at | C1QA | complement component 1, q subcomponent, alpha polypeptide | 150 | 26 | 1.7 | 0.9 | 1.5 | 1.0 | 1.2 |
| 208594_x_at | LILRB3 | leukocyte immunoglobulin-like receptor, subfamily B, member 3 | 117 | 12 | 1.7 | 0.9 | 1.1 | 1.0 | 1.4 |
| 209348_s_at | MAF | v-maf musculoaponeurotic fibrosarcoma oncogene homolog (avian) | 280 | 67 | 1.7 | 1.0 | 1.3 | 0.9 | 0.9 |
| 201999_s_at | TCTEL1 | t-complex-associated-testis-expressed 1-like 1 | 785 | 133 | 1.7 | 0.9 | 1.0 | 0.9 | 0.9 |
| 204924_at | TLR2 | toll-like receptor 2 | 100 | 26 | 1.7 | 0.9 | 0.8 | 0.8 | 1.4 |
| 210176_at | TLR1 | toll-like receptor 1 | 68 | 18 | 1.7 | 0.9 | 1.3 | 0.8 | 1.3 |
| 202902_s_at | CTSS | cathepsin S | 276 | 38 | 1.6 | 1.0 | 1.2 | 1.1 | 1.3 |
| 208829_at | TAPBP | TAP binding protein (tapasin) | 318 | 51 | 1.6 | 0.9 | 1.1 | 1.1 | 1.0 |
| 202638_s_at | ICAM1 | intercellular adhesion molecule 1 (CD54), human rhinovirus receptor | 256 | 83 | 1.6 | 0.8 | 0.8 | 0.9 | 1.5 |
| 212203_x_at | IFITM3 | interferon induced transmembrane protein 3 (1-8U) | 1101 | 194 | 1.6 | 1.4 | 1.1 | 1.0 | 1.3 |
| 200905_x_at | HLA-E | major histocompatibility complex, class I, E | 1308 | 239 | 1.6 | 1.3 | 1.1 | 1.2 | 1.2 |
| 203923_s_at | CYBB | cytochrome b-245, beta polypeptide | 183 | 20 | 1.6 | 0.9 | 1.2 | 1.0 | 1.2 |
| 204747_at | IFIT4 | interferon-induced protein with tetratricopeptide repeats 4 | 123 | 21 | 1.6 | 0.9 | 0.8 | 0.9 | 0.9 |
| 209687_at | CXCL12 | chemokine (C—X—C motif) ligand 12 (stromal cell-derived factor 1) | 1071 | 254 | 1.6 | 1.0 | 1.1 | 0.8 | 1.3 |
| 211332_x_at | HFE | hemochromatosis | 134 | 13 | 1.6 | 1.0 | 0.8 | 1.1 | 0.9 |
| 211866_x_at | HFE | hemochromatosis | 154 | 25 | 1.6 | 1.0 | 0.9 | 1.2 | 0.9 |
| 201859_at | PRG1 | proteoglycan 1, secretory granule | 683 | 182 | 1.5 | 0.8 | 1.2 | 0.9 | 1.2 |
| 203932_at | HLA-DMB | major histocompatibility complex, class II, DM beta | 331 | 43 | 1.5 | 1.1 | 1.4 | 1.2 | 1.0 |
| 202450_s_at | CTSK | cathepsin K (pycnodysostosis) | 415 | 68 | 1.5 | 1.3 | 1.0 | 1.2 | 1.3 |
| 203416_at | CD53 | CD53 antigen | 296 | 119 | 1.5 | 1.2 | 2.3 | 1.0 | 1.4 |
| 213932_x_at | HLA-A | major histocompatibility complex, class I, A | 1373 | 131 | 1.5 | 1.2 | 1.3 | 1.2 | 1.1 |
| 208992_s_at | STAT3 | signal transducer and activator of transcription 3 (acute-phase response factor) | 698 | 120 | 1.5 | 1.0 | 1.0 | 1.0 | 1.1 |
| 219118_at | FKBP11 | FK506 binding protein 11, 19 kDa | 184 | 39 | 1.5 | 0.6 | 1.0 | 0.8 | 0.8 |
| 210559_s_at | CDC2 | cell division cycle 2, G1 to S and G2 to M | 89 | 20 | 1.5 | 1.0 | 1.3 | 1.0 | 1.2 |
| 218856_at | TNFRSF21 | tumor necrosis factor receptor super-family, member 21 | 407 | 63 | 1.5 | 1.2 | 1.5 | 1.1 | 1.2 |
| 209049_s_at | PRKCBP1 | protein kinase C binding protein 1 | 314 | 40 | 1.5 | 1.0 | 1.2 | 0.9 | 1.0 |
| 213193_x_at | TRB@ | T cell receptor beta locus | 214 | 67 | 1.5 | 1.2 | 2.4 | 1.2 | 1.2 |
| 204118_at | CD48 | CD48 antigen (B-cell membrane protein) | 225 | 42 | 1.5 | 1.1 | 1.7 | 1.0 | 1.2 |
| 209753_s_at | TMPO | thymopoietin | 110 | 41 | 1.5 | 0.8 | 0.9 | 0.9 | 1.1 |

TABLE 1-continued

The most discriminant genes for Vioxx animal #A60055 and corresponding genomics expression data from iliac vein samples of monkeys treated with vehicle, Vioxx ®, Celebrex ®, Cox189 (Novartis), and diclofenac. These results indicated potential vasculopathies in the animal A60055, probably induced by an unknown virus infection together with an exaggerated host immune response against vascular endothelium.

| Systematic Name | SYMBOL | GENENAME | Control Avg | Control SD | Vioxx A60055 | Vioxx without A60055 | Celebrex | Cox189 | Voltaren |
|---|---|---|---|---|---|---|---|---|---|
| | | | | | | Avg fold changes vs control | | | |
| 200887_s_at | STAT1 | signal transducer and activator of transcription 1, 91 kDa | 92 | 12 | 1.5 | 1.2 | 1.1 | 1.3 | 1.1 |
| 203561_at | FCGR2A | Fc fragment of IgG, low affinity IIa, receptor for (CD32) | 128 | 46 | 1.5 | 1.1 | 1.4 | 0.8 | 1.4 |
| 209734_at | HEM1 | hematopoietic protein 1 | 196 | 24 | 1.5 | 1.2 | 1.5 | 1.0 | 1.1 |
| AFFX-HU-MISGF3A/M97935_3_at | STAT1 | signal transducer and activator of transcription 1, 91 kDa | 51 | 11 | 1.4 | 1.1 | 1.1 | 1.3 | 1.0 |
| 204852_s_at | PTPN7 | protein tyrosine phosphatase, non-receptor type 7 | 39 | 23 | 1.4 | 1.4 | 2.0 | 1.0 | 1.4 |
| 211799_x_at | HLA-C | major histocompatibility complex, class I, C | 1978 | 1219 | 1.4 | 1.0 | 1.0 | 1.5 | 0.8 |
| 204232_at | FCER1G | Fc fragment of IgE, high affinity I, receptor for; gamma polypeptide | 513 | 73 | 1.4 | 0.9 | 1.3 | 1.0 | 1.5 |
| 218831_s_at | FCGRT | Fc fragment of IgG, receptor, transporter, alpha | 1066 | 183 | 1.4 | 1.0 | 1.0 | 1.0 | 0.9 |
| 216231_s_at | B2M | beta-2-microglobulin | 9970 | 1299 | 1.4 | 1.2 | 1.3 | 1.1 | 1.2 |
| 219117_s_at | FKBP11 | FK506 binding protein 11, 19 kDa | 772 | 157 | 1.4 | 0.7 | 0.8 | 0.7 | 0.7 |
| 217733_s_at | TMSB10 | thymosin, beta 10 | 8296 | 1670 | 1.4 | 1.1 | 1.1 | 1.1 | 1.2 |
| 203922_s_at | CYBB | cytochrome b-245, beta polypeptide (chronic granulomatous disease) | 70 | 22 | 1.4 | 1.2 | 1.7 | 0.9 | 1.1 |
| 203729_at | EMP3 | epithelial membrane protein 3 | 400 | 35 | 1.4 | 0.7 | 0.9 | 0.8 | 0.8 |
| 205298_s_at | BTN2A2 | butyrophilin, subfamily 2, member A2 | 259 | 22 | 1.4 | 1.1 | 1.2 | 1.3 | 1.1 |
| 220336_s_at | GP6 | glycoprotein VI (platelet) | 39 | 14 | 1.4 | 1.2 | 1.1 | 1.2 | 1.0 |
| 200904_at | HLA-E | major histocompatibility complex, class I, E | 700 | 284 | 1.4 | 1.1 | 1.2 | 1.0 | 1.2 |
| 205831_at | CD2 | CD2 antigen (p50), sheep red blood cell receptor | 71 | 18 | 1.4 | 1.1 | 1.5 | 1.1 | 1.1 |
| 205098_at | CCR1 | chemokine (C-C motif) receptor 1 | 82 | 21 | 1.4 | 1.1 | 0.9 | 0.8 | 1.3 |
| 215990_s_at | BCL6 | B-cell CLL/lymphoma 6 (zinc finger protein 51) | 295 | 32 | 1.3 | 1.0 | 0.9 | 1.4 | 1.0 |
| 210514_x_at | HLA-A | major histocompatibility complex, class I, A | 1046 | 84 | 1.3 | 1.2 | 1.1 | 1.2 | 1.0 |
| 213869_x_at | THY1 | Thy-1 cell surface antigen | 318 | 97 | 1.3 | 0.8 | 0.8 | 0.9 | 0.6 |
| 202637_s_at | ICAM1 | intercellular adhesion molecule 1 (CD54), human rhinovirus receptor | 429 | 54 | 1.3 | 0.8 | 0.9 | 1.0 | 1.0 |
| 202957_at | HCLS1 | hematopoietic cell-specific Lyn substrate 1 | 174 | 17 | 1.3 | 1.2 | 1.5 | 1.0 | 1.1 |
| 209749_s_at | ACE | angiotensin I converting enzyme 1 | 76 | 25 | 1.3 | 0.9 | 0.8 | 0.8 | 1.1 |
| 210915_x_at | TRB@ | T cell receptor beta locus | 176 | 34 | 1.3 | 1.3 | 2.5 | 1.3 | 1.0 |
| 209048_s_at | PRKCBP1 | protein kinase C binding protein 1 | 176 | 22 | 1.3 | 1.3 | 1.2 | 1.1 | 1.0 |
| 221978_at | HLA-F | major histocompatibility complex, class I, F | 66 | 15 | 1.3 | 1.3 | 1.2 | 1.4 | 1.4 |
| 210904_s_at | IL13RA1 | interleukin 13 receptor, alpha 1 | 354 | 81 | 1.2 | 1.1 | 0.9 | 1.1 | 0.9 |
| 203879_at | PIK3CD | phosphoinositide-3-kinase, catalytic, delta polypeptide | 160 | 25 | 1.2 | 1.1 | 1.7 | 1.1 | 1.3 |
| 204158_s_at | TCIRG1 | T-cell, immune regulator 1, ATPase, H+ transporting, lysosomal V0 protein a isoform 3 | 163 | 37 | 1.2 | 1.0 | 0.9 | 1.0 | 1.0 |
| 52940_at | SIGIRR | single Ig IL-1R-related molecule | 142 | 32 | 1.2 | 1.1 | 1.2 | 0.9 | 1.0 |

The strongest increase has been observed in veins (e.g., 20-fold for CXCL10 in pulmonary vein) and adrenal followed by arteries and heart tissues. Much less and irrelevant changes were observed in samples from liver, kidney, GIT, spleen, BM and cartilage. The fact that specific histopathological vascular findings have been observed only in veins and the genomic data show the presence of the specific pattern in all of the CV tissues tested, suggest that the genomic pattern (particularly, some soluble factors e.g., CXCL10 and CCL2) may be considered as early biomarkers for cox-2 inhibition-related CV side-effects or as early biomarkers for minimal (sub-clinical) vasculitis.

Vioxx® exhibits increased angiostatic and focal inflammatory effects predominantly in veins: The in vivo angiogenic effect of PGE2 is well documented experimentally and in particular by the fact that the EP4 receptor signalling has a major role in regulating closure or maintaining potency of the ductus arteriosus in newborns with congenital heart disease. Apart from this expected inhibition of angiogenic effects of PGE2 by coxibs tested in this analysis, Vioxx® strongly induced the expression of CXCL10, and PD-ECGF (both known anti-angiogenic proteins) mainly in iliac and pulmonary veins which suggests that a strong angiostatic effect occurred in the monkey #A60055.

The specific gene expression pattern observed in the monkey treated with Vioxx® strongly suggests the involvement of an endothelial cell tropic CMV-like infection or reactivation: (i) The expression of numbers of genes inducible by INFγ was strongly upregulated in most of the tissues from the Vioxx®-treated monkey. According to the literature, the induction of INFγ pathway is commonly observed during the first phase of CMV infection or reactivation. It has been shown that CMV antigen-stimulated CD4+ T cells from normal healthy CMV-seropositive donors secreted INFγ and TNF alpha, driving chemokines induction in endothelial cells. The strong INFγ pathway induction and histopathological findings of focal vasculitis in animal #A60055 together with the literature data indicate that latent endothelial cell tropic CMV infection might induces specific cellular immune responses, resulting in the induction of chemoatractants, leading to inflammation and endothelial cell injury. Bolovan-Fritts C A et al., *J Virol.* 78(23):13173-81 (December 2004).

(ii) In the vessels of the monkey A60055, expression of chemokines, mainly CXCL10, MCP-1 and at a lesser degree other chemokines e.g., CXCL9 and -11 were significantly upregulated (e.g., 150 fold increase for MCP-1 in pulmonary vein). It has been shown that atheroma-associated endothelial cells express CXCL10, CXCL9 and CXCL11. Their secretion from IFNγ-stimulated ECs is increased upon IL-1beta, TNF-alpha, and CD40 ligand treatments and decreased in the presence of nitric oxide. Mach F et al., *J Clin Invest.* 104(8):1041-50 (October 1999). These data suggest the involvement of these cytokines/chemokines in the pathogenesis/progression of inflammatory vascular changes such as arteriosclerosis or vasculitis. More interestingly, mouse CMV infection in an atherosclerosis animal model and in cholesterol-fed C57BL/6J mice significantly increases atherosclerotic lesion area and aortic expression of CXCL10, MCP-1, and other INF-gamma induced proteins. Burnett M S et al., *Circulation.* 109(7):893-7 (Feb. 24, 2004). Similarly, mouse CMV infection in the brains of immunodeficient mice, stimulates the production of CXCL10 and MCP-1. Cheeran M C et al., *J Neurovirol.* 10(3):152-62 (June 2004).

In light of these data, our results suggest that an endothelial cell tropic CMV-like reactivation might be the main factor involved in the initiation of the observed vascular changes in this analysis. Interestingly, human CMV encodes four chemokine receptors e.g., US28, which bind many of the human CC-chemokines, including RANTES, MCP-1, CCL3, and CXCL-11. As mentioned above, this class of chemokines contributes to the development of vascular disease such as atherosclerosis, restenosis, and transplant vascular sclerosis. The increased expression of these chemokines genes and/or their respective receptors (TABLE 1) in the monkey treated with Vioxx® raises the question whether they were produced by reactivated CVM virions or by INFγ activated endothelial cells as a result of inflammatory reaction to CMV infection.

Literature data also demonstrate that the induction of COX-2 and/or synthesis of PGE2 are essential for efficient CMV replication in human (Zhu H et al., *Proc. Natl. Acad. Sci. USA* 99:3932-3937 (2002)) and monkey (Rue C A et al., *J Virol.* 78(22):12529-36 (November 2004)). Interestingly, the rhesus cytomegalovirus (RhCMV) genome encodes a protein homologue to cellular cox-2 (vCOX-2). Experiments with vCOX-2 deleted RhCMV identified vCOX-2 as a critical determinant for endothelial cell tropism. Rue C A et al., *J Virol.* 78(22):12529-36 (November 2004).

The cPLA2, a key enzyme in arachidonic acid (AA) release, is the primary form of PLA2 responsible for the generation of PGE2, LTB4 and PAF from AA, in response to inflammatory stimuli. It has been established that cPLA2 exhibits antihypertrophic potential probably via signalling pathway of β2-ARs in heart. Pavoine C & Defer N, *Cell Signal.* 17(2):141-52 (February 2005). PLA2 signalling pathways has been shown to be involved in human CMV infection in several ways. (i) hCMV infection stimulates arachidonic acid metabolism associated with activation of PLA2 and a cellular cPLA2, (ii) both mRNAs encoding for cPLA2 and COX-2 are increased in infected cells, (iii) blocking the cellular pathway of PLA2 signalling inhibited hCMV infection, and recently (iv) it has been reported that a cPLA2 taken up by virus particles from infected cells plays a role in CMV infection at a post entry step. The inhibition of hCMV-borne cPLA2 had broader consequences on HCMV infection inhibiting the production of key viral antigens IE1, IE2 and pp65. In this monkey analysis, expression of cPLA2 was upregulated in most of the cardiovascular tissues from the Vioxx®-treated monkey only. Since all other monkeys showed no increase of cPLA2 expression, these data also suggest the presence/reactivation of a CMV infection in the endothelial cell of the Vioxx®-treated monkeys.

CMV is known as a strictly opportunistic pathogen, in immunocompetent individuals it is easily controlled yet never eliminated since a robust immune response suppresses persistent viral replication and facilitates a lifelong viral latency. In fact, CMV has several mechanisms to escape diverse host immune responses. CMV encodes for at least four proteins which interfere with classical MHC class I antigen presentation by preventing their cell surface expression, by transporting them to the cytosol, where they are degraded and by competing with TAP for the translocation of antigenic peptides to MHC molecules. However, evasion of MHC I is not perfect, since IFNγ activation by CMV can induce the synthesis of large quantities of MHC I and proteosomes that overwhelm viral inhibitory proteins and "rescue" the CTL response. Two CMV-encoded proteins also interact with non-classical MHC class I such as HLA-E, which leads to suppression of NK responses. CMV encode for the UL18 which has homology to MHC I heavy chain and is expressed on the cell surface. Disruption of UL18 severely restricts viral pathogenesis. CMV also interferes with MHC II presentation, which was strongly upregulated in the Vioxx®-treated monkey (TABLE 1). Classically, INF-gamma is a potent inducer of MHC II expression in many cell types including endothelial cells. However, some studies showed that in CMV-infected cells, IFN-gamma is unable to induce MHC II expression. Recently, MHC class II molecules expressed in EC have been proposed as the entry receptor for CMV. Thus, the protein expression of MHC class II molecules in tissue samples will be tested whether their increased mRNA expression are translated into functional proteins. CMV infection also induces alteration in the expression of important cytokines such as TNF, IGF beta and IL1 and upregulation of the complement control proteins CD46, and CD55. CMV also encodes for a surface Fc-receptor which can bind IgG with high affinity. Interestingly, expression of most of these genes including MHC molecules, several NK cell receptors, complement proteins, Fc receptors was significantly upregulated in the monkey #A60055. These results support the hypothesis that the specific expression pattern is probably induced by a CMV infection in the animal A60055 (TABLE 1).

The expression of Toll like receptor 2 and CD14 was significantly increased in several tissues from the Vioxx®-treated monkey. Recently, it has been shown that CMV activates inflammatory cytokine responses via TLR2/CD14 during the prereplication phase of the viral life cycle. Indeed, interferon and ISGs are robustly induced by CMV particles during entry via activation of IRF3, one of the key transcription factors for INFγ inducible genes. Later during the replication cycle, CMV encodes several chemokines and chemokine receptors that provide potent inflammatory signals. In fact, many of the pathological processes associated with CMV reactivation (including accelerated vascular disease, and graft rejection) appear to be mediated by the release of inflammatory cytokines. Compton T et al., *J Virol.* 77(8):4588-96 (April 2003). Even though other viruses (measles virus, and RSV), also activate innate responses in a TLR2/CD14-dependent manner, the overall expression pattern suggests that CMV infection/reactivation is probably responsible for the observed vasculitis in the veins of the Vioxx®-treated monkey.

CMV reactivation in the vascular system and use of anti-inflammatory compounds including NSAIDs and specific Cox-2 inhibitors: A number of infectious agents have been associated with atherosclerotic cardiovascular disorders, including CMV, *Helicobacter pylori,* EBV, HIV, HSV1, HSV2, and hepatitis B and C. Rue C A et al., *J Virol.* 78(22):12529-36 (November 2004). However, several reports in the literature suggest that the CMV infection/reactivation might be one of the major players in the pathogenesis of chronic inflammatory vascular diseases. For examples, rare cases of CMV vasculitis have been described even in healthy individuals, which may be associated with carotid intimal-medial thickening, or development of extensive mesenteric arterial and venous thrombosis. Other studies suggest that CMV infection or reactivation is involved in post-transplant sub endothelium/intramyocardial inflammation, atherogenesis, restenosis, and inflammatory abdominal aortic aneurysm. Koskinen P K et al., *Transpl Infect Dis.* 1(2):115-26 (June 1999)). Since ECs are one of the major targets for latent CMV infection, CMV induced lytic or inflammatory reaction in ECs may easily result in adherent thrombi formation in vivo. Thus, infection/reactivation of CMV in endothelial cells may cause vascular injury and promote the development of inflammation, atherosclerotic lesions, and thrombosis. Therefore, the observed vascular findings in this analysis might be the early indicators of a CMV vasculitis.

In line with our current observations on Vioxx® CV effect, Rott D et al., *J Am Coll Cardiol.* 41(10):1812-9 (May 21, 2003) found that inhibition of Cox-2 aggravated atherosclerosis in the apoE knockout mouse. The authors studied the effect of COX-2 inhibition on infectivity of cytomegalovirus and coincidentally showed increased disease burden in animals treated with the COX-2 inhibitor, including those not infected with the virus. According to the FitzGerald hypothesis (see BACKGROUND OF THE INVENTION), this should reflect selective suppression of PGI2 and an unopposed effect of TXA2, however, the authors suggest an alternative hypothesis indicating that the suppression of anti-inflammatory PGs, such as PGJ2, and its metabolite 15-deoxy-delta12,14-PGJ2 might also result in this type of vascular changes. Rott D et al., *J Am Coll Cardiol.* 41(10): 1812-9 (May 21, 2003). Another hypothesis might be that Cox-2 specific inhibitors but also NSAIDs can also initiate or aggravate atherosclerotic changes by inhibiting the production of PGE2 leading to the reactivation of latent CMV infection. In fact, it has been clearly documented that PGE2 can inhibit replication of viruses including CMV and HIV-1 through activation of cAMP and PKA which are the key enzymes in the negative regulation of immune responses and a potential target for inhibiting autoreactive T cells. Aandahl E M et al., *J. Immunol.* 169(2):802-8 (Jul. 15, 2002). Other reports support this hypothesis showing that PGE-2 suppresses chemokine production by increasing cAMP trough the EP4 receptor. Takayama K et al., *J Biol Chem.*277(46): 44147-54 (Nov. 15, 2002). It has been shown that PGE2 activated cAMP/PKA inhibits INFγ signalling pathway proteins (JAK-1 and STAT1) and consequently decrease chemokine synthesis such as CXCL10. Kanda N et al., *J Invest Dermatol.* 119(5):1080-9 (November 2002).

More interestingly, a selective cox-2 inhibitor, NS398, potentiates CXCL10 synthesis upon INFγ stimulation by preventing PGE2 production and PKA activation. Wright K L et al., *Br J Pharmacol.* 141(7):1091-7 (April 2004). In our analysis, the significant activation of numbers of INFγ inducible genes even in vascular tissues where there was no histopathological abnormalities suggest that Vioxx® has similar potentialization effect on the INFγ pathway activation as described for NS398. Thus, the Vioxx® treatment might lower the threshold for the generation of a chronic vascular inflammation via inhibition of PGE2 and activation of INFγ pathways triggered by reactivation of a latent CMV infection in endothelial cells. It is noteworthy that the CMV seropositivity has been reported in most of the monkey strains and in about 60-70% of healthy individuals. Overall, the data suggest that inhibition of Cox-2 and in particular PGE2 by Vioxx® might results in an uncontrollable/continuous production of soluble factors induced by INFγ pathway activation. The INFγ pathway is commonly induced in case of endothelial/vascular tropic virus infection including some isolates of CMV. As suggested by the presently observed findings, activation of vascular endothelium and attraction of specific blood cells by chemokines (e.g., CXCL10, MCP-1, often activated during a CMV infection) might increase their interaction leading to cardiovascular adverse effects.

The histopathological examination revealed marginal vascular changes consistent with the genomic findings and suggesting that the specific genomic pattern is an early signature of vasculitis and is observed only in the monkey treated with Vioxx® (FIG. 3).

Figure 5:
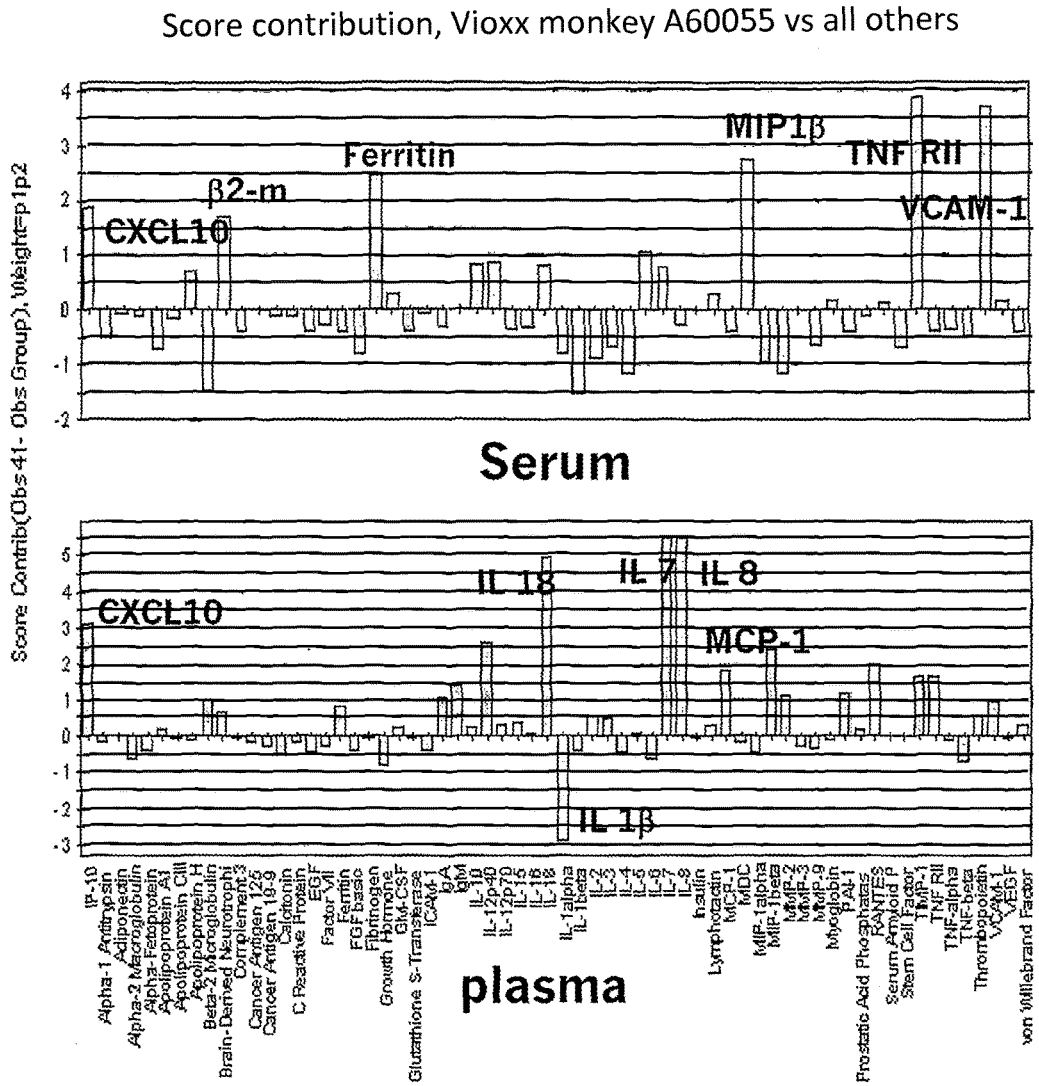
FIG. 5. Protein profiling in serum and plasma from the monkeys. The monkey #A60055 exhibit a specific protein expression profile: Soluble MHC molecules b2-m, other chemokines, cytokines (INFγ, CXCL10, MCP-1, IL18, TNF RII, IL1b), and soluble VCAM-1. Human MAP is used to assess monkey proteins in a Rules-Based Medicine (RBM®) multiplex assay.

Soluble proteins present in serum and plasma of the same monkeys have been measured using a multiplex assay produced by Rules-Based Medicine (RBM®) of Texas. The results were in line with the genomic results showing the increased level of INFγ inducible proteins only in the Vioxx®-treated monkey (FIG. 5).

Figure 6:
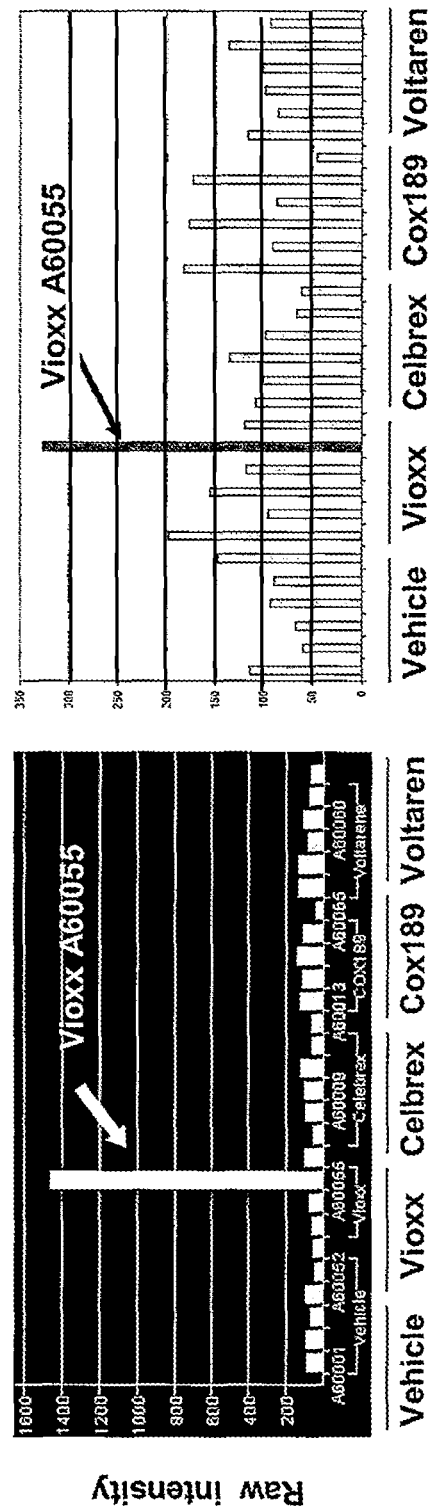
FIG. 6. ELISA confirmation of CXCL10 (IP10) protein level in monkey serum samples. The Vioxx®-treated monkey #A60055 exhibits the highest level of CXCL10 protein expression.
Figure 7:
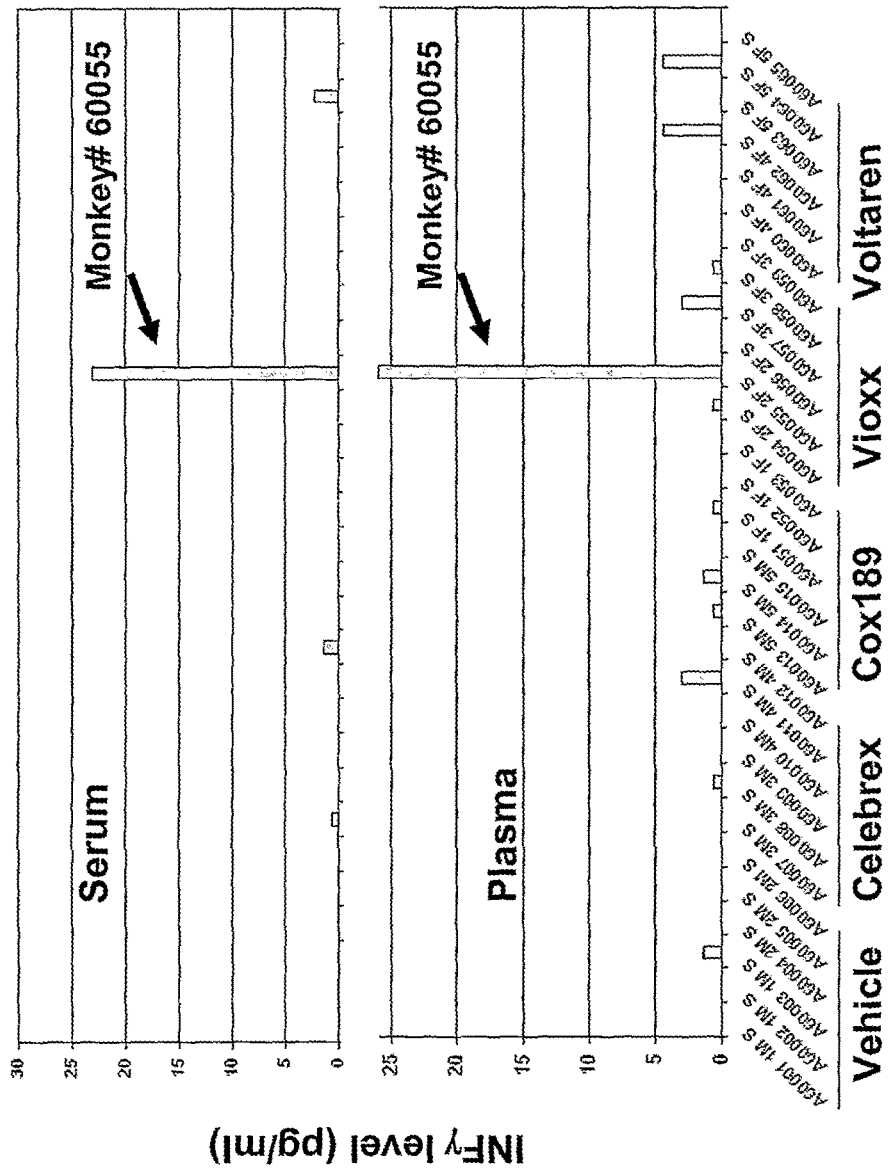
FIG. 7. ELISA confirmation of INFγ protein level in monkey serum and plasma samples. The Vioxx®-treated monkey #A60055 exhibits the highest level of INFγ protein expression.

Increased expression of CXCL10 chemokine and INFγ has been confirmed by an ELISA both in serum and plasma from the Vioxx®-treated monkey (FIG. 6 and FIG. 7). These peripheral biomarkers might allow safe use of cox-2 inhibitory compounds in clinics and selection of cox-2 inhibitory follow-up compounds without cardiovascular toxicity.

Figure 8:
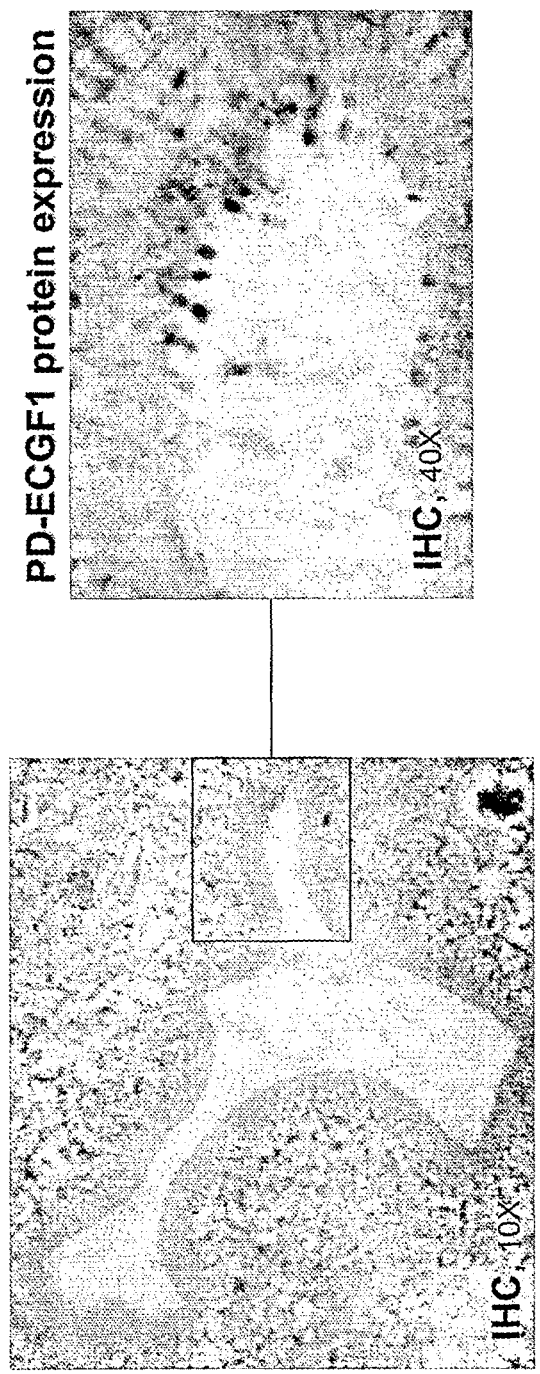
FIG. 8. Localisation of PD-ECGF1 protein at the site of vascular lesion.

Localisation of several proteins (e.g., PD-ECGF1) at the site of vascular lesion indicates the specificity of changes for a vasculopathy (FIG. 8). The genomic and serum/plasma protein signature identified in this analysis predicts for a minimal and focal vasculitis and may be used for patient's monitoring of vasculitis induced by different compounds/drugs (e.g., phosphodiesterase inhibitors) or occurring during vascular or autoimmune disorders.

Conclusion: Overall genomic data showed that the Vioxx®-treated animals, and in particular the animal #60055 exhibit a specific mRNA expression pattern which strongly suggest the induction of an intravascular procoagulative/prothrombotic state particularly in venous vessels of the Vioxx®-treated animals. The specific genomics pattern includes genes involved in blood and endothelial cell activation, interaction between blood and ECs, strong activation of INFγ pathway, and release of pro-inflammatory cytokines and chemo-attractants. These data together with biochemical and histopathological findings suggest that Vioxx® may exaggerate host immune response during some/specific viral infection(s) with endothelial tropism, suggestively reactivation of a CMV infection.

Our hypothesis is that the inhibition of Cox-2/PGE2 results in decreased level of cAMP and PKA and consequently in an uncontrollable/continuous production of soluble factors via INFγ pathways induced by a CMV infection in endothelial/blood cells. Activation of vascular endothelium and attraction of specific blood cells by chemokines should further increase their interaction leading to prothrombotic events and increasing the risk of cardiovascular adverse events. Indeed, the majority of these changes have been shown to be directly involved in the pathogenesis of diverse cardiovascular diseases including atherosclerosis, CAD, and thrombosis. Preliminary histopathological results confirmed the genomic finding showing that the specific genomics pattern is an early signature of vasculitis and observed only in the animal(s) treated with Vioxx®.

Identification of biomarkers might allow the safe use of cox-2 inhibitory compounds in clinics and selection of cox-2 inhibitory follow-up compounds without cardiovascular toxicity. Indeed, several of the gene increases in the vessels of the Vioxx®-treated animal encode for secreted proteins, e.g., CXCL10, other chemokines, which can be measured in peripheral samples such as blood or urine. If a CMV reactivation (or other endothelium tropic virus infection) is confirmed, a vaccination strategy prior to administration of Cox-2 inhibitory therapies might be an alternative approach for improving the CV therapeutic and safety profile of this class of compounds.

REFERENCES

Aandahl E M, Moretto W J, Haslett P A, Vang T, Bryn T, Tasken K, Nixon D F. Inhibition of antigen-specific T cell proliferation and cytokine production by protein kinase A type I. *J Immunol.* 2002 Jul. 15; 169(2):802-8.

AbuBakar, S., I. Boldogh, and T. Albrecht. 1990. Human cytomegalovirus stimulates arachidonic acid metabolism through pathways that are affected by inhibitors of phospholipase A2 and protein kinase C. *Biochem. Biophys. Res. Commun.* 166:953-959.

AbuBakar, S., I. Boldogh, and T. Albrecht. 1990. Human cytomegalovirus. Stimulation of [$^3$H] release from [$^3$H]-arachidonic acid prelabelled cells. *Arch. Virol.* 113:255-266.

Alcami, A., and U. H. Koszinowski. 2000. Viral mechanisms of immune evasion. *Trends Microbiol.* 8:410-418.

Altschul, S. F., T. L. Madden, A. A. Schaffer, J. Zhang, Z. Zhang, W. Miller, and D. J. Lipman. 1997. Gapped BLAST and PSI-BLAST: a new generation of protein database search programs. *Nucleic Acids Res.* 25:3389-3402.

Baek, S. H., J. Y. Kwak, S. H. Lee, T. Lee, S. H. Ryu, D. J. Uhlinger, and J. D. Lambeth. 1997. Lipase activities of p37, the major envelope protein of vaccinia virus. *J. Biol. Chem.* 272:32042-32049.

Bairoch, A. 2000. The ENZYME database in 2000. *Nucleic Acids Res.* 28:304-305.

Baron M, D. N. Streblow, N. Mirouze, J. A. Nelson, J-L Davignon. Optimization of the CD4+ T cell response to an epitope of the HCMV IE1 protein.

Blasco, R., and B. Moss. 1991. Extracellular vaccinia virus formation and cell-to-cell virus transmission are prevented by deletion of the gene encoding the 37,000-dalton outer envelope protein. *J. Virol.* 65:5910-5920.

Bordier, C. 1981. Phase separation of integral membrane proteins in Triton X-114 solution. *J. Biol. Chem.* 256: 1604-1607.

Bresnahan, W. A., and T. Shenk. 2000. A subset of viral transcripts packaged within human cytomegalovirus particles. *Science* 288:2373-2376.

Brown, W. J., K. Chambers, and A. Doody. 2003. Phospholipase A2 (PLA2) enzymes in membrane trafficking: mediators of membrane shape and function. *Traffic* 4:214-221.

Buono C, Pang H, Uchida Y, Libby P, Sharpe A H, Lichtman A H. B7-1/B7-2 costimulation regulates plaque antigen-specific T-cell responses and atherogenesis in low-density lipoprotein receptor-deficient mice. *Circulation.* 2004 Apr. 27; 109(16):2009-15.

Burnett M S, Durrani S, Stabile E, Saji M, Lee C W, Kinnaird T D, Hoffman E P, Epstein S E. Murine cytomegalovirus infection increases aortic expression of proatherosclerotic genes. *Circulation.* 2004 Feb. 24; 109(7):893-7.

Carr D J, Chodosh J, Ash J, Lane T E. Effect of anti-CXCL10 monoclonal antibody on herpes simplex virus type 1 keratitis and retinal infection. *J Virol.* 2003 September; 77(18):10037-46.

Cheeran M C, Gekker G, Hu S, Min X, Cox D, Lokensgard J R. Intracerebral infection with murine cytomegalovirus induces CXCL10 and is restricted by adoptive transfer of splenocytes. *J Neurovirol.* 2004 Jun.; 10(3): 152-62.

Cipollone F, Fazia M, Iezzi A, Zucchelli M, Pini B, De Cesare D, Ucchino S, Spigonardo F, Bajocchi G, Bei R, Muraro R, Artese L, Piattelli A, Chiarelli F, Cuccurullo F, Mezzetti A. Suppression of the functionally coupled cyclooxygenase2/prostaglandin E synthase as a basis of simvastatin-dependent plaque stabilization in humans. *Circulation.* 2003 Mar. 25; 107(11):1479-85.

Claudel-Renard, C., C. Chevalet, T. Faraut, and D. Kahn. 2003. Enzyme-specific profiles for genome annotation: PRIAM. *Nucleic Acids Res.* 31:6633-6639.

Compton T, Kurt-Jones E A, Boehme K W, Belko J, Latz E, Golenbock D T, Finberg R W. Human cytomegalovirus activates inflammatory cytokine responses via CD14 and Toll-like receptor 2. *J Virol.* 2003 April; 77(8):4588-96.

Das, A., L. Asatryan, M. A. Reddy, C. A. Wass, M. F. Stins, S. Joshi, J. V. Bonventre, and K. S. Kim. 2001. Differential role of cytosolic phospholipase A2 in the invasion of brain microvascular endothelial cells by *Escherichia coli* and *Listeria monocytogenes*. *J. Infect. Dis.* 184:732-737.

Dewald O, Ren G, Duerr G D, Zoerlein M, Klemm C, Gersch C, Tincey S, Michael L H, Entman M L, Frangogiannis N G. Of mice and dogs: species-specific differences in the inflammatory response following myocardial infarction. *Am J Pathol.* 2004 February; 164(2): 665-77.

Fitzgerald G A. Coxibs and cardiovascular disease. *N Engl J Med.* 2004 Oct. 21; 351(17):1709-11.

Fortunato, E. A., A. K. McElroy, I. Sanchez, and D. H. Spector. 2000. Exploitation of cellular signaling and regulatory pathways by human cytomegalovirus. *Trends Microbial.* 8:111-119.

Frangogiannis N G, Mendoza L H, Lewallen M, Michael L H, Smith C W, Entman M L. Induction and suppression of interferon-inducible protein 10 in reperfused myocardial infarcts may regulate angiogenesis. *FASEB J.* 2001 Jun.; 15(8):1428-30.

Furberg C D, Psaty B M, FitzGerald G A. Parecoxib, valdecoxib, and cardiovascular risk. *Circulation.* 2005 Jan. 25; 111(3):249.

Girod, A., C. E. Wobus, Z. Zadori, M. Ried, K. Leike, P. Tijssen, J. A. Kleinschmidt, and M. Hallek. 2002. The VP1 capsid protein of adeno-associated virus type 2 is carrying a phospholipase A2 domain required for virus infectivity. *J. Gen. Viral.* 83:973-978.

Gomez-Marin, J. E., H. El'Btaouri, A. Bonhomme, F. Antonicelli, N. Pezzella, H. Burlet, D. Aubert, I. Villena, M. Guenounou, B. Haye, and J. M. Pinon. 2002. Involvement of secretory and cytosolic phospholipases A2 during infection of THP1 human monocytic cells with *Toxoplasma gondii*. Effect of interferon gamma. *Parasitol. Res.* 88:208-216.

Gravel S.-P. and Servant M. J. Roles of an IkappaB Kinase-related Pathway in Human Cytomegalovirus-infected Vascular Smooth Muscle Cells: a molecular link in pathogen-induced proatherosclerotic conditions. *J. Biol. Chem.,* 280(9): 7477-7486 (Mar. 4, 2005).

Greijer, A. E., C. A. J. Dekkers, and J. M. Middeldorp. 2000. Human cytomegalovirus virions differentially incorporate viral and host cell RNA during the assembly process. *J. Virol.* 74:9078-9082.

Hakes, D. J., K. J. Martell, W. G. Zhao, R. F. Massung, 3. J. Esposito, and J. E. Dixon. 1993. A protein phosphatase related to the vaccinia virus VH1 is encoded in the genomes of several orthopoxviruses and a baculovirus. *Proc. Natl. Acad. Sci. USA* 90:4017-4021.

Hansen S G, Strelow L I, Franchi D C, Anders D G, Wong S W. Complete sequence and genomic analysis of rhesus cytomegalovirus. *J Virol.* 2003 June; 77(12): 6620-36.

Hendrickson, H. S. 1994. Fluorescence-based assays of lipases, phospholipases, and other lipolytic enzymes. *Anal. Biochem.* 219:1-8.

Hillyer P, Mordelet E, Flynn G, Male D. Chemokines, chemokine receptors and adhesion molecules on different human endothelia: discriminating the tissue-specific functions that affect leucocyte migration. *Clin Exp Immunol.* 2003 December; 134(3):431-41.

Hirabayashi, T., and T. Shimizu. 2000. Localization and regulation of cytosolic phospholipase $A_2$. *Biochim. Biophys. Acta* 1488:124-138.

Hsai D A, Mitra S K, Hauck, Streblow D N, Nelson J A, Ilic D, Huang S, Li E, Nemerow G R, Leng J, Spencer K S R, Cheresh D A, Schlaepfer. Differential regulation of cell motility and invasion by FAK. *J Cell Biol.* 160:753-767 (2003).

Ilim D, Kovanin B, Yohkura K, Schlaepfer, Tomacevim N, Han Q, Kim J-B, Howerton, K, Baumbusch C, Ogiwara N, Streblow D, Nelson J A, Dazin P, Shino Y, Sasaki K, and Damsky C H. FAK is required for normal fibronectin matrix assembly. *J. Cell Science:* 117:177-187 (2003).

Ishiguro N, Takada A, Yoshioka M, Ma X, Kikuta H, Kida H, Kobayashi K. Induction of interferon-inducible protein-10 and monokine induced by interferon-gamma from human endothelial cells infected with Influenza A virus. *Arch Virol.* 2004 January; 149(1):17-34.

Kahl M, Siegel-Axel D, Stenglein S, Jahn G, Sinzger C. Efficient lytic infection of human arterial endothelial cells by human cytomegalovirus strains. *J Virol.* 2000 August; 74(16):7628-35.

Kanda N, Watanabe S. Cyclooxygenase-2 inhibitor enhances whereas prostaglandin E2 inhibits the production of interferon-induced protein of 10 kDa in epidermoid carcinoma A431. *J Invest Dermatol.* 2002 November; 119(5): 1080-9.

Kawamura A, Miura S, Fujino M, Nishikawa H, Matsuo Y, Tanigawa H, Tomita S, Tsuchiya Y, Matsuo K, Saku K. CXCR3 chemokine receptor-plasma IP10 interaction in patients with coronary artery disease. *Circ J.* 2003 October; 67(10):851-4.

Kemken, D., K. Mier, H. A. Katus, G. Richardt, and T. Kurz. 2000. A HPLC-fluorescence detection method for determination of cardiac phospholipase D activity in vitro. *Anal. Biochem.* 286:277-281.

Landini, M. P., and A. Ripalti. 1982. A DNA-nicking activity associated with the nucleocapsid of human cytomegalovirus. *Arch. Virol.* 73:351-356.

Le Roy, E., M. Baron, W. Faigle, D. Clement, D. M. Lewinsohn, D. N. Streblow, J. A. Mach F, Sauty A, Iarossi A S, Sukhova G K, Neote K, Libby P, Luster A D. Differential expression of three T lymphocyte-activating CXC chemokines by human atheroma-associated cells. *J Clin Invest.* 1999 October; 104(8):1041-50.

Mar, E. C., P. C. Patel, and E. S. Huang. 1981. Human cytomegalovirus-associated DNA polymerase and protein kinase activities. *J. Gen. Virol.* 57:149-156.

Melnychuk R M, D N. Streblow, P Smith, A J Hirsch, D. Pancheva, Nelson J A. The human cytomegalovirus encoded G-protein coupled receptor US28 mediates smooth muscle cell migration through G12. *J. Virol.* 78: 8382-9391 (2004).

Michelson, S., P. Turowski, L. Picard, J. Goris, M. P. Landini, A. Topilko, B. Hemmings, C. Bessia, A. Garcia, and J. L. Virelizier. 1996. Human cytomegalovirus carries serine/threonine protein phosphatases PP1 and a host-cell derived PP2A. *J. Virol.* 70:1415-1423.

Nakai Y, Iwabuchi K, Fujii S, Ishimori N, Dashisoodol N, Watano K, Mishima T, Iwabuchi C, Tanaka S, Bezbradica J S, Nakayama T, Taniguchi M, Miyake S, Yamamura T, Kitabatake A, Joyce S, Van Kaer L, Onoe K. Natural killer T cells accelerate atherogenesis in mice. *Blood.* 2004 Oct. 1; 104 (7):2051-9.

Namiki M, Kawashima S, Yamashita T, Ozaki M, Sakoda T, Inoue N, Hirata K, Morishita R, Kaneda Y, Yokoyama M. Intramuscular gene transfer of interleukin-10 cDNA reduces atherosclerosis in apolipoprotein E-knockout mice. *Atherosclerosis.* 2004 January; 172 (1):21-9.

Nelson, S. Amigorena, and J. L. Davignon. 2002. Infection of APC by human cytomegalovirus controlled through recognition of endogenous nuclear immediate early protein 1 by specific $CD4^+$ T lymphocytes. *J. Immunol.* 169:1293-1301.

Nokta, M. A., M. I. Hassan, K. Loesch, and R. B. Pollard. 1996. Human cytomegalovirus-induced immunosuppression. Relationship to tumor necrosis factor-dependent release of arachidonic acid and prostaglandin E2 in human monocytes. *J. Clin. Investig.* 97:2635-2641.

Orloff, S. L., D N. Streblow, C. Soderberg-Naucler, Q. Yinl, C. Kreklywich, C. L. Corless, P. A. Smith, C. Loomis, L. Mills, J. W. Cook T. De La Melena2, C. A. Bruggeman, J. A. Nelson, and C. R. Wagner. 2001. Elimination of Donor-specific Alloreactivity Prevents virus-accelerated Chronic Rejection in Rat Small Bowel and Heart Transplants. *Transplant Proc;* 33(1-2):1822-3 (2001).

Pace, J., M. J. Hayman, and J. E. Galan. 1993. Signal transduction and invasion of epithelial cells by *S. typhimurium*. *Cell* 72:505-514.

Pass, R. F. 2001. *Cytomegalovirus*, p. 2675-2706. In P. M. Howley and D. M. Knipe (ed.), *Fields virology*. Lippincott, Williams and Wilkins, Philadelphia, Pa.

Pavoine C, Defer N. The cardiac beta2-adrenergic signalling a new role for the cPLA2. *Cell Signal*. 2005 Feb.; 17(2):141-52.

Pickard, R. T., B. A. Strifler, R. M. Kramer, and J. D. Sharp. 1999. Molecular cloning of two new human paralogs of 85-kDa cytosolic phospholipase A2. *J. Biol. Chem*, 274:8823-8831.

Reddehase, M. J. 2002. Antigens and immunoevasins: opponents in cytomegalovirus immune surveillance. *Nat. Rev. Immunol*. 2:831-844.

Rott D, Zhu J, Burnett M S, Zhou Y F, Zalles-Ganley A, Ogunmakinwa J, Epstein S E. Effects of MF-tricyclic, a selective cyclooxygenase-2 inhibitor, on atherosclerosis progression and susceptibility to cytomegalovirus replication in apolipoprotein-E knockout mice. *J Am Coll Cardiol*. 2003 May 21; 41(10):1812-9.

Rott D, Zhu J, Zhou Y F, Burnett M S, Zalles-Ganley A, Epstein S E. IL-6 is produced by splenocytes derived from CMV-infected mice in response to CMV antigens, and induces MCP-1 production by endothelial cells: a new mechanistic paradigm for infection-induced atherogenesis. *Atherosclerosis*. 2003 October; 170(2):223-8.

Rue C A, Jarvis M A, Knoche A J, Meyers H L, DeFilippis V R, Hansen S G, Wagner M, Fruh K, Anders D G, Wong S W, Barry P A, Nelson J A. A cyclooxygenase-2 homologue encoded by rhesus cytomegalovirus is a determinant for endothelial cell tropism. *J Virol*. 2004 November; 78(22):12529-36.

Shibutani, T., T. M. Johnson, Z. X. Yu, V. J. Ferrans, J. Moss, and S. E. Epstein. 1997. Pertussis toxin-sensitive G proteins as mediators of the signal transduction pathways activated by cytomegalovirus infection of smooth muscle cells. *J. Clin. Investig*. 100:2054-2061.

Six, D. A., and E. A. Dennis. 2000. The expanding superfamily of phospholipase $A_2$ enzymes: classification and characterization. *Biochim. Biophys. Acta* 1488:1-19.

Soderberg-Naucler, C., D. Streblow, K. N. Fish, J Allan-Yorke, and J. A. Nelson. IFN-γ dependent reactivation of human cytomegalovirus (HCMV) in allogeneically stimulated macrophages. *J. Virol* 75(16):7543-54 (2001).

Spear, G. T., N. S. Lurain, C. J. Parker, M. Ghassemi, G. H. Payne, and M. Saifuddin. 1995. Host cell-derived complement control proteins CD55 and CD59 are incorporated into the virions of two unrelated enveloped viruses. Human T cell leukemia/lymphoma virus type I (HTLV-I) and human cytomegalovirus (HCMV). *J. Inzmunol*. 155:4376-4381.

Streblow D N, Kreklywich C, Yin Q, De La Melena V T, Corless C L, Smith P A, Brakebill C, Cook J W, Vink C, Bruggeman C A, Nelson J A, Orloff S L. Cytomegalovirus-mediated upregulation of chemokine expression correlates with the acceleration of chronic rejection in rat heart transplants. *J Virol* 77:2182-2194 (2003).

Streblow D N, Orloff S L, and J. A. Nelson. Do pathogens accelerate atherosclerosis *J Nutr*. 2001 October; 131(10):2798S-804S.

Streblow D N, Orloff S L, Nelson J A. The HCMV Chermokine Receptor US28 is a potential target in vascular disease. *Curr Drug targets Infect Disord* 1:151-158 (2001).

Streblow D N, Vomaske J, Smith P, Melnychuk R, Hall L, Pancheva D, Schlaephler D A, and Nelson J A. The Human Cytomegalovirus Chemokine Receptor US28 Activates Focal Adhesion Kinase In A Ligand Dependent Manner. *J. Biol. Chem* 278(50):50456-65 (2003).

Streblow, D. N., C. Soderberg-Naucler, J. Vieira, P. Smith, E. Wakabayashi, F. Ruchti, K. Mattison, Y. Altschuler, and J. A. Nelson. The human cytomegalovirus chemokine receptor US28 mediates vascular smooth muscle cell migration. *Cell* 99: 511-520 (1999).

Takayama K, Garcia-Cardena G, Sukhova G K, Comander J, Gimbrone M A Jr, Libby P. Prostaglandin E2 suppresses chemokine production in human macrophages through the EP4 receptor. *J Biol Chem*. 2002 Nov. 15; 277(46):44147-54.

Tanaka, J., T. Ogura, H. Iida, H. Sato, and M. Hatano. 1988. Inhibitors of prostaglandin synthesis inhibit growth of human cytomegalovirus and reactivation of latent virus in a productively and latently infected human cell line. *Virology* 163:205-208.

Tatapudi R, Muthukumar T, Dadhania D, Ding R, Li B, Sharma V K, Lozada-Pastorio E, Seetharamu N, Hartono C, Serur D, Seshan S V, Kapur S, Hancock W, Suthanthiran M. Noninvasive detection of renal allograft inflammation by measurements of mRNA for IP-10 and CXCR3 in urine. *Kidney Int*. 2004 June; 65(6):2390-7.

Tay S, McCormack A, Rose M L. Effect of cognate human CD4+ T cell and endothelial cell interactions upon chemokine production. *Transplantation*. 2004 Oct. 15; 78(7):987-94.

Tsunoda I, Lane T E, Blackett J, Fujinami R S. Distinct roles for IP-10/CXCL10 in three animal models, Theiler's virus infection, EAE, and MHV infection, for multiple sclerosis: implication of differing roles for IP-10. *Mult Scler*. 2004 Feb.;10(1):26-34.

Vliegen I, Duijvestijn A, Stassen F, Bruggeman C. Murine cytomegalovirus infection directs macrophage differentiation into a pro-inflammatory immune phenotype: implications for atherogenesis. *Microbes Infect*. 2004 Oct.; 6(12):1056-62.

Wright K L, Weaver S A, Patel K, Coopman K, Feeney M, Kolios G, Robertson D A, Ward S G. Differential regulation of prostaglandin E biosynthesis by interferon-gamma in colonic epithelial cells. *Br J Pharmacol*. 2004 April; 141(7):1091-7.

Wright, J. F., A. Kurosky, E. L. G. Pryzdial, and S. Wasi. 1995. Host cellular annexin II is associated with cytomegalovirus particles isolated from cultured human fibroblasts. *J. Virol*. 69:4784-4791.

Zadori, Z., J. Szelei, M. C. Lacoste, Y. Li, S. Gariepy, P. Raymond, M. Allaire, I. R. Nabi, and P. Tijssen. 2001. A viral phospholipase A2 is required for parvovirus infectivity. *Dev. Cell* 1:291-302.

Zhu, H., J. P. Cong, D. Yu, W. A. Bresnahan, and T. E. Shenk. 2002. Inhibition of cyclooxygenase 2 blocks human cytomegalovirus replication. *Proc. Natl. Acad. Sci. USA* 99:3932-3937.

Zhu, H., J. P. Cong, G. Mamtora, T. Gingeras, and T. Shenk. 1998. Cellular gene expression altered by human cytomegalovirus: global monitoring with oligonucleotide arrays. *Proc. Natl. Acad. Sci. USA* 95:14470-14475.

All references cited herein are incorporated herein by reference in their entirety and for all purposes to the same extent as if each individual publication or patent or patent application was specifically and individually indicated to be incorporated by reference in its entirety for all purposes. In addition, all Affymetrix identification numbers for each probe set corresponding to each gene changes cited herein (TABLE 1) are incorporated herein by reference in their entirety and for all purposes to the same extent as if each such number was specifically and individually indicated to be incorporated by reference in its entirety for all purposes.

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatus within the scope of the invention, in addition to those enumerated herein, will be apparent to those skilled in the art from the foregoing description and accompanying drawings. Such modifications and variations are intended to fall within the scope of the appended claims. The present invention is to be limited only by the terms of the appended claims, along with the full scope of equivalents to which such claims are entitled.

What is claimed:

1. A method for determining if a subject has early vasculitis or other vasculopathies, said method comprising:
    (a) obtaining a plasma or serum sample from a human subject to whom a compound or drug, susceptible to induce cardiovascular pathologies has been administered or a subject with a vascular autoimmune disorder;
    (b) detecting the presence of a biomarker of minimal or early vasculitis or other vasculopathies in the plasma or serum sample; and
    wherein the biomarker of minimal or early vasculitis or other vasculopathies is selected from the group consisting of b2-m, INFγ, IL-18, TNF-RII, CCL2, CXCL-9, CXCL-10, CXCL-11, soluble VCAM-1, and combinations thereof;
    (c) determining whether the subject has minimal or early vasculitis or other vasculopathies based upon the presence or absence of a biomarker of minimal or early vasculitis or other vasculopathies; and
    wherein the biomarker is measured using multiplex and/or multianalyte assays to measure the biomarker.

2. A method for determining if a subject has cox-2 inhibitor-induced cardiovascular adverse effects, where the subject has been administered a cox-2 inhibitory compound or drug, comprising the steps of:
    (a) obtaining a plasma or serum sample from a human subject to whom a cox-2inhibitory compound or drug has been administered;
    (b) detecting the presence of a biomarker of cardiovascular adverse effects in the plasma or serum sample; and
    wherein the biomarker of cardiovascular effects is selected from the group consisting of b2-m, INFγ, IL-18, TNF-RII, CCL2, CXCL-9, CXCL-10, CXCL-11, soluble VCAM-1, and combinations thereof;
    (c) determining whether the subject has cox-2 inhibitor-induced cardiovascular adverse effects based upon the presence or absence of a biomarker of cardiovascular adverse effects; and
    wherein the biomarker is measured using multiplex and/or multianalyte assays to measure the biomarker.

3. The method of claim 2, wherein the cox-2 inhibitor compound or drug is selected from the group consisting of: celecoxib, rofecoxib and lumiracoxib (COX 189).

* * * * *